US010506929B2

(12) United States Patent
Almoumen

(10) Patent No.: US 10,506,929 B2
(45) Date of Patent: Dec. 17, 2019

(54) ANESTHETIC SYRINGE WITH A NERVE DETECTOR

(71) Applicant: Imam Abdulrahman Bin Faisal University, Dammam (SA)

(72) Inventor: Saud Abdullah Almoumen, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

(21) Appl. No.: 15/497,869

(22) Filed: Apr. 26, 2017

(65) Prior Publication Data

US 2018/0310954 A1    Nov. 1, 2018

(51) Int. Cl.
| | |
|---|---|
| *A61B 5/00* | (2006.01) |
| *A61M 5/20* | (2006.01) |
| *A61M 5/178* | (2006.01) |
| *A61M 5/24* | (2006.01) |
| *A61M 5/31* | (2006.01) |
| *A61B 17/34* | (2006.01) |
| *A61B 90/00* | (2016.01) |

(Continued)

(52) U.S. Cl.
CPC .......... *A61B 5/0075* (2013.01); *A61B 5/0068* (2013.01); *A61B 5/4893* (2013.01); *A61B 17/3401* (2013.01); *A61B 90/37* (2016.02); *A61M 5/178* (2013.01); *A61M 5/20* (2013.01); *A61M 5/24* (2013.01); *A61M 5/3134* (2013.01); *A61B 5/40* (2013.01); *A61B 5/489* (2013.01); *A61B 17/3403* (2013.01); *A61M 5/343* (2013.01); *A61M 19/00* (2013.01); *A61M 2005/3125* (2013.01); *A61M 2005/31588* (2013.01); *A61M 2202/048* (2013.01); *A61M 2205/3306* (2013.01); *A61M 2205/3327* (2013.01); *A61M 2205/3331* (2013.01); *A61M 2205/3584* (2013.01); *A61M 2205/502* (2013.01); *A61M 2205/587* (2013.01)

(58) Field of Classification Search
CPC ... A61M 19/00; A61M 5/427; A61B 17/3403; A61B 5/0059; A61B 5/0075; A61B 5/40; A61B 5/4893; A61B 5/05; A61B 5/4887; A61B 2090/378; A61B 8/085; A61B 8/08; A61B 8/0833; A61B 90/37; A61B 2017/3413; A61B 5/04001; A61B 5/4041; A61B 5/053
See application file for complete search history.

(56) References Cited

U.S. PATENT DOCUMENTS

| | | | | |
|---|---|---|---|---|
| 1,495,924 | A | * | 5/1924 | Quale ..................... A61M 5/24 604/232 |
| 3,448,277 | A | * | 6/1969 | Jayko ................. G01N 21/8507 250/573 |

(Continued)

*Primary Examiner* — Bhisma Mehta
*Assistant Examiner* — Hong-Van N Trinh
(74) *Attorney, Agent, or Firm* — Oblon, McClelland, Maier & Neustadt, L.L.P.

(57) ABSTRACT

An anesthetic syringe comprising a nerve detector and an illuminated indicator. The nerve detector is configured to receive a radiative energy from a nerve in a tissue and send a signal to the illuminated indicator. The illuminated indicator shows a direction to move the syringe to a tissue location proximal to the nerve for injecting a local anesthetic drug. The syringe may accommodate a standard drug cartridge and may provide manual or automatic movement of a plunger.

12 Claims, 8 Drawing Sheets

(51) Int. Cl.
*A61M 5/34* (2006.01)
*A61M 19/00* (2006.01)
*A61M 5/315* (2006.01)

(56) References Cited

U.S. PATENT DOCUMENTS

| | | | | |
|---|---|---|---|---|
| 5,719,700 | A * | 2/1998 | Corcuff | A61B 5/0068 359/211.5 |
| 5,800,360 | A * | 9/1998 | Kisner | G08B 13/19 600/532 |
| 5,813,987 | A * | 9/1998 | Modell | A61B 5/0062 250/216 |
| 8,852,111 | B2 * | 10/2014 | Park | A61B 8/0833 600/407 |
| 2004/0064101 | A1 * | 4/2004 | Kowan | A61M 5/14546 604/189 |
| 2004/0158205 | A1 * | 8/2004 | Savage | A61M 5/007 604/151 |
| 2010/0114023 | A1 * | 5/2010 | Francis | A61B 5/0059 604/116 |
| 2011/0060229 | A1 * | 3/2011 | Hulvershorn | A61B 5/0215 600/486 |
| 2012/0143056 | A1 * | 6/2012 | Slayton | A61B 8/4254 600/439 |
| 2013/0041258 | A1 * | 2/2013 | Patrick | A61B 8/00 600/439 |
| 2013/0165904 | A1 | 6/2013 | Hadzic | |
| 2013/0261533 | A1 | 10/2013 | Norkunas | |
| 2014/0316225 | A1 * | 10/2014 | Clendenen | A61B 5/1455 600/314 |
| 2015/0208934 | A1 | 7/2015 | Sztrubel et al. | |
| 2016/0228645 | A1 | 8/2016 | Patrick et al. | |
| 2017/0245943 | A1 * | 8/2017 | Foster | A61B 34/20 |

* cited by examiner

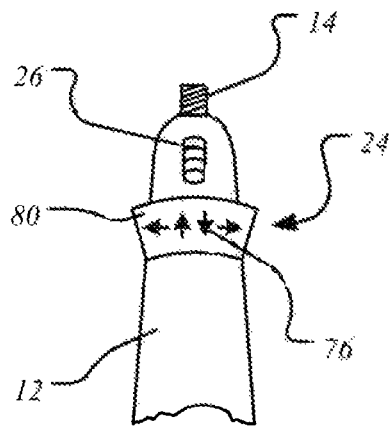
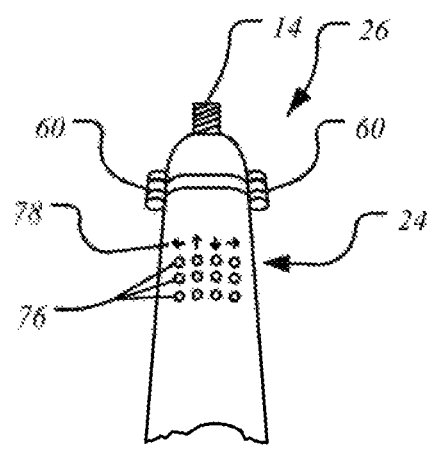
FIG. 5A  FIG. 5B
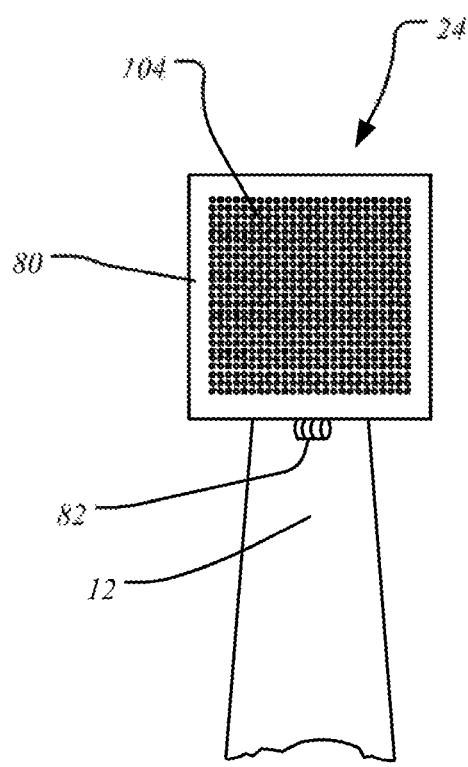
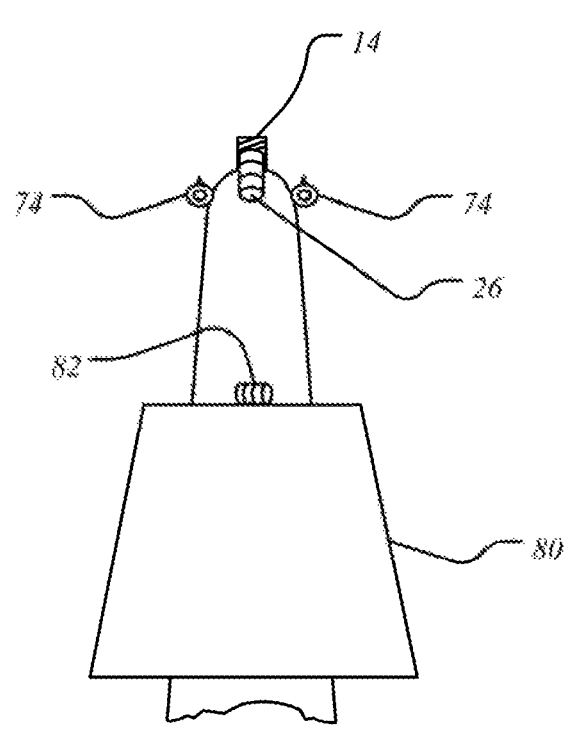
FIG. 5C  FIG. 5D

ANESTHETIC SYRINGE WITH A NERVE DETECTOR

BACKGROUND OF THE INVENTION

Technical Field

The present invention relates to an anesthetic syringe that has a nerve detector to detect a radiative energy from a nerve.

Description Of The Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

In performing a nerve block or local anesthetic injection, a medical professional will inject an anesthetic drug into the tissue of a patient at a location where the anesthetic effect is most desired. Generally, this injection site is close to a major nerve, in which the anesthetic affects the major nerve and thus anesthetizes downstream minor nerves. Injecting in such an optimal location allows for a greater influence of the drug. However, locating such an optimal location remains challenging for a medical professional, as the exact location of major nerves differs from patient to patient. To further complicate this matter, the medical professional furthermore must avoid neural tissue spearing or injecting into a blood vessel, both of which lead to unintended outcomes for a patient.

Some technologies currently exist for viewing nerves and may be used to guide an anesthetic injection. For instance, nerves may be imaged by CT scan or MRI, however, given the confines of the imaging apparatus, a nerve block injection cannot easily be performed in tandem. After imaging, the data collected from a CT scan or MRI may be too complex for a medical professional to interpret in terms of specific locations of nerves. In addition, some medical offices, and especially dental offices, might not have access to CT or MRI equipment.

Another technique, image guided anesthesia, is in use for viewing and locating major nerves. Here ultrasonography imaging is used to find an optimal injection site in real-time. However, this technique involves two separate handheld instruments (the ultrasonography probe and the syringe), and may be too cumbersome to use in some locations, such as a patient's mouth.

Lastly, some methods of direct electrical stimulation have been proposed for locating nerves for optimal anesthetic injections. However, this requires electrical leads in direct contact with the patient and may cause risk for patients with electronic medical implants, such as pacemakers. Also, these methods do not create a direct mapping of a nerve's location, and where the syringe needle or other needles are used as electrical leads, a risk of neural tissue sparing or harming the nerves with electric current still exists.

In view of the forgoing, one objective of the present invention is to provide a syringe to detect a radiative energy from a nerve to determine a location proximal to a nerve to receive art anesthetic injection.

BRIEF SUMMARY OF THE INVENTION

According to a first aspect, the present disclosure relates to an anesthetic syringe that has a hollow syringe barrel with a needle mount extending outwards from a first end of the barrel a plunger extending from a second end of the barrel and slidably moveable within the barrel, the plunger having a piston-engaging tip extending into the barrel, an illuminated indicator attached to an exterior part of the barrel, and a nerve detector attached to a second exterior part of the barrel or to the illuminated indicator. The illuminated indicator is electrically connected to the nerve detector, and the illuminated indicator is configured to both receive a signal from the nerve detector and indicate at least one direction to move the anesthetic syringe to deliver an anesthetic injection proximal to a nerve.

In one embodiment, the anesthetic syringe has a spectrometer attached to a side of the barrel, and the spectrometer is configured to detect blood in an aspirate.

In another embodiment, the anesthetic syringe with the spectrometer has a second illuminated indicator on an exterior side of the barrel. This second illuminated indicator is electrically connected to the spectrometer to indicate if blood has been detected during aspiration.

In one embodiment, the nerve detector of the anesthetic syringe is attached to the illuminated indicator.

In one embodiment, the anesthetic syringe has a transmitter configured to emit a radiative energy onto the nerve.

In a further embodiment, the anesthetic syringe with the transmitter has the transmitter attached to the illuminated indicator.

In one embodiment, the anesthetic syringe does not have a transmitter.

In one embodiment, the illuminated indicator on the anesthetic syringe is slidably and/or pivotally attached to the barrel.

In one embodiment, the nerve detector of the anesthetic syringe comprises at least one focusing lens.

In one embodiment, the nerve detector of the anesthetic syringe comprises two or more photodetectors.

In one embodiment the nerve detector of the anesthetic syringe comprises at least one rotatable and/or pivotable reflector configured to direct an incoming radiative energy.

In a further embodiment, where the nerve detector has at least one rotatable and/or pivotable reflector, the nerve detector also has an adjustable pinhole.

In one embodiment, the nerve detector of the anesthetic syringe has a Nipkow disk rotatably attached to and encircling the syringe barrel. This Nipkow disk has a plurality of pinholes and is configured to direct rays of an incoming radiative energy to at least one photodetector.

In one embodiment, the illuminated indicator comprises a first display panel mounted to an arm attached to the barrel.

In a further embodiment, where the illuminated indicator comprises a first display panel mounted to an arm attached to the barrel, the display panel comprises at least 625 LEDs.

In another further embodiment, where the illuminated indicator comprises a first display panel mounted to an arm attached to the barrel, the arm is removably attached to the barrel.

In another further embodiment, where the illuminated indicator comprises a first display panel mounted to an arm attached to the barrel, the first display panel is positioned outwards from the first end of the barrel and shaped to accommodate a needle attached and extending outwards from the needle mount.

In another further embodiment where the illuminated indicator comprises a first display panel mounted to an arm attached to the barrel, the illuminated indicator further comprises a second display panel mounted to a second arm attached to the barrel.

In a further embodiment, where the illuminated indicator comprises a first display panel mounted to an arm attached to the barrel and a second display panel mounted to a second arm and attached to the barrel, both display panels are shaped to accommodate a needle attached and extending outwards from the needle mount.

According to a second aspect, the present disclosure relates to a method of administering a nerve block to a nerve in a patient using the anesthetic syringe of the first aspect. This method involves receiving a radiative energy from a nerve by the nerve detector, indicating a direction to move the anesthetic syringe to a location of a tissue proximal to the nerve by the illuminated indicator, moving the syringe to the location of the tissue proximal to the nerve, inserting a needle mounted onto the needle mount of the anesthetic syringe into the location of the tissue proximal to the nerve, where the anesthetic syringe is loaded with a drug cartridge comprising an anesthetic drug, and performing an anesthetic injection of the anesthetic drug.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 5A is a portion of an anesthetic syringe having arrows as an illuminated indicator.

FIG. 5B is a portion of an anesthetic syringe having an illuminated indicator comprising labels and lights.

FIG. 5C is a portion of an anesthetic syringe having an LED display on a display panel hingedly attached to the syringe barrel.

FIG. 5D is the anesthetic syringe in FIG. 5C with the display panel folded down.

DETAILED DESCRIPTION OF THE EMBODIMENTS

Figure 1A:
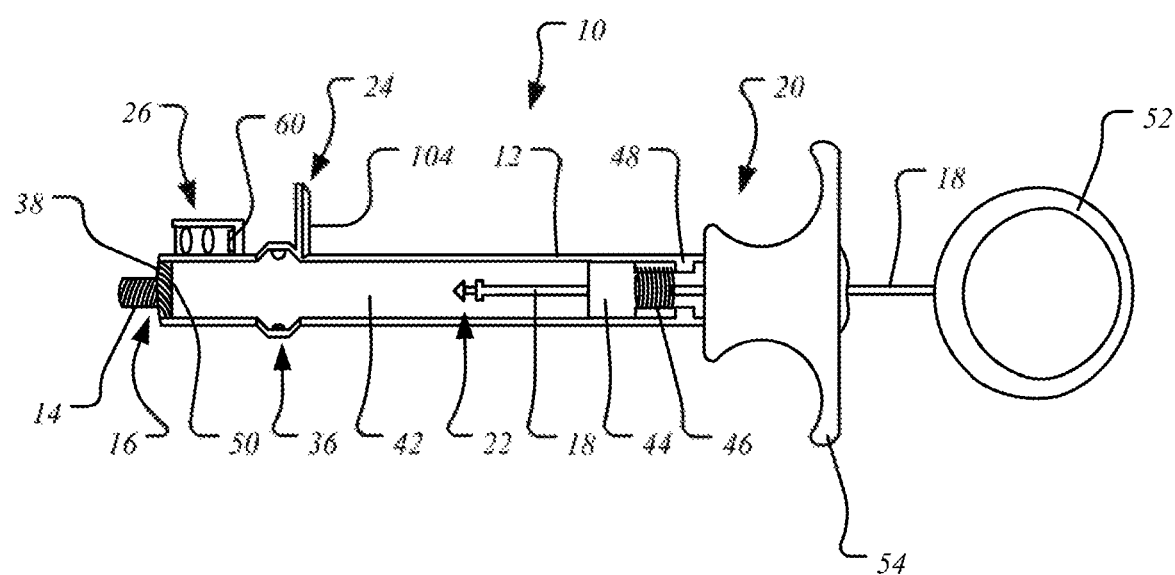
FIG. 1A is a side section view of an anesthetic syringe with a nerve detector and spectrometer.

Embodiments of the present disclosure will now be described more fully hereinafter with reference to the accompanying drawings, in which some, but not all embodiments of the disclosure are shown. In the drawings, like reference numerals designate identical or corresponding parts throughout the several views.

The present disclosure will be better understood with reference to the following definitions. As used herein, the words "a" and "an" and the like carry the meaning of "one or more." Within the description of this disclosure, where a numerical limit or range is stated, the endpoints are included unless stated otherwise. Also, all values and subranges within a numerical limit or range are specifically included as if explicitly written out.

As used herein, the term "nerve" is considered synonymous with the following terms: neural tissue, neural cells, neural tissue cells, neurons of the central and/or peripheral nervous systems, or bundles of neurons.

According to a first aspect, the present disclosure relates to an anesthetic syringe 10 that has a hollow syringe barrel 12 with a needle mount 14 extending outwards from a first end of the barrel 16, a plunger 18 extending from a second end of the barrel 20 and slidably moveable within the barrel, the plunger having a piston-engaging tip 22 extending into the barrel, an illuminated indicator 24 attached to an exterior part of the barrel, and a nerve detector 26 attached to a second exterior part of the barrel or to the illuminated indicator 24. The illuminated indicator is electrically connected to the nerve detector, configured to both receive a signal from the nerve detector; and indicate at least one direction to move the anesthetic syringe to deliver an anesthetic injection proximal to a nerve.

The hollow syringe barrel 12 may be a cylinder with a diameter of 6-12 mm, preferably 7-11 mm, more preferably 7-10 mm and a length of 50-100 mm, preferably 60-80 mm, more preferably 60-70 mm. The sidewall of the syringe barrel may have a thickness of 0.5-4 mm, preferably 0.7-2 mm, more preferably 0.8-1.2 mm. The sidewall, as well as other parts of the anesthetic syringe, may comprise a biocompatible metal, such as stainless steel, aluminum, cobalt, zirconium, titanium, or some other metal. However, non-metals may be used such as polylactic acid (PLA), poly (lactic-co-glycolic acid) (PLGA), polyvinylchloride (PVC), polyethylene terephthalate (PET), acrylonitrile butadiene styrene (ABS), polypropylene (PP), polystyrene (PS), polytetrafluoroethylene (PTFE), polyetheretherketone (PEEK), polyetherketoneketone (PEKK), polycarbonate (PC), glass, carbon fiber, and/or ceramic. Preferably the barrel is sterilizable by autoclave or other means. In some embodiments, the syringe may comprise an additional casing in order to contain mechanical parts, such as an electric motor and/or gears. In other embodiments, an additional casing 28 may provide a hand grip or electrical switches 126 for the syringe. In a related embodiment, a syringe may have a hand grip casing which is removably attached, and the syringe may be used with or without the hand grip easing in place.

In a preferred embodiment the interior of the hollow syringe barrel 12, or the space between the needle mount 14 and the piston-engaging tip 22 of the plunger, is cylindrical and configured to accommodate a standard drug cartridge. The drug cartridge may be used in the injection of local anesthetics for dental and oral procedures. As used herein, the term anesthetic includes any pharmaceutical, medicament, formulation and/or any other fluid, substance or material that causes anesthesia or a loss of sensation. Anesthetics also include drugs that partially destroy nervous tissue. In other embodiments, the syringe may be used for regional anesthesia, peripheral anesthesia, local anesthesia, or nerve block procedures involving injection of one or more anesthetic drugs or other drugs that otherwise influence nerve tissue. Anesthetic drugs include, but are not limited to cocaine, procaine, chloroprocaine, tetracaine, lidocaine, mepivacaine, bupivacaine, etidocaine, prilocaine, and/or levonordefrin. In other embodiments the syringe may be used for injection into a tissue outside of the patient's mouth, for example, in the patient's shoulder, forearm, wrist, thigh, foot, spine, neck, jaw, or an internal organ. In one embodiment, a drug cartridge may contain at least one anesthetic drug and at least one non-anesthetic drug, such as epinephrine. However, in other embodiments, the drug cartridge may include drug or drugs that are not anesthetic, such as steroids, and the syringe may be used in other medical procedures that require an injection, such as a vaccination. In one embodiment, the syringe may be used with non-human animals. In another embodiment, the drug cartridge may be used solely for aspiration, for instance, collecting cells and/or biological fluids for a biopsy, a lab test, or a drug test. Preferably the syringe may accommodate a standard 1.8 mL drug cartridge, and in some embodiments the syringe may be able to accommodate a standard 1 mL drug cartridge, a standard 2.2 mL drug cartridge, and/or other sizes. Preferably the drug cartridge is a transparent glass or plastic cylinder with one end closed by an elastomeric stopper or piston, and with the opposite end comprising an opening sealed with an elastomeric membrane or septum. Preferably the cartridge has a sidewall thickness of 0.8-1.2 mm. In an alternative embodiment, the plunger may comprise a piston that seals against the interior walls of the hollow syringe barrel. In that embodiment, the hollow syringe barrel may be filled directly with a drug solution, without using a drug cartridge or other secondary container.

Figure 1B:
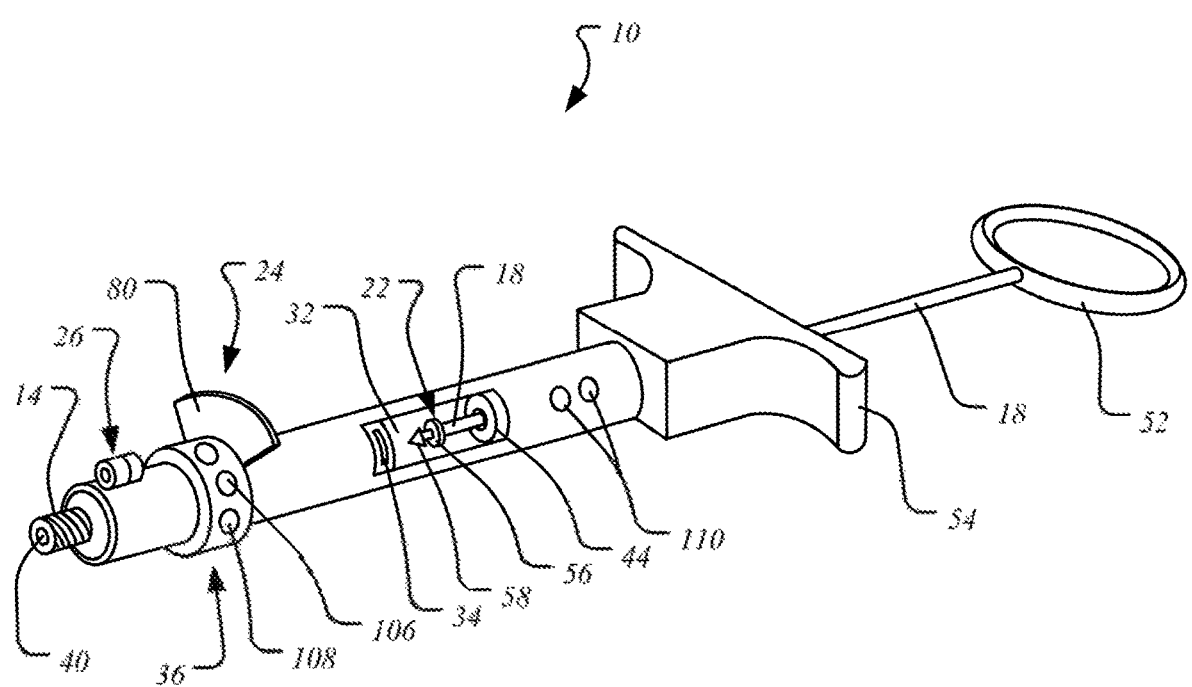
FIG. 1B is a perspective view of the anesthetic syringe in FIG. 1A.
Figure 2:
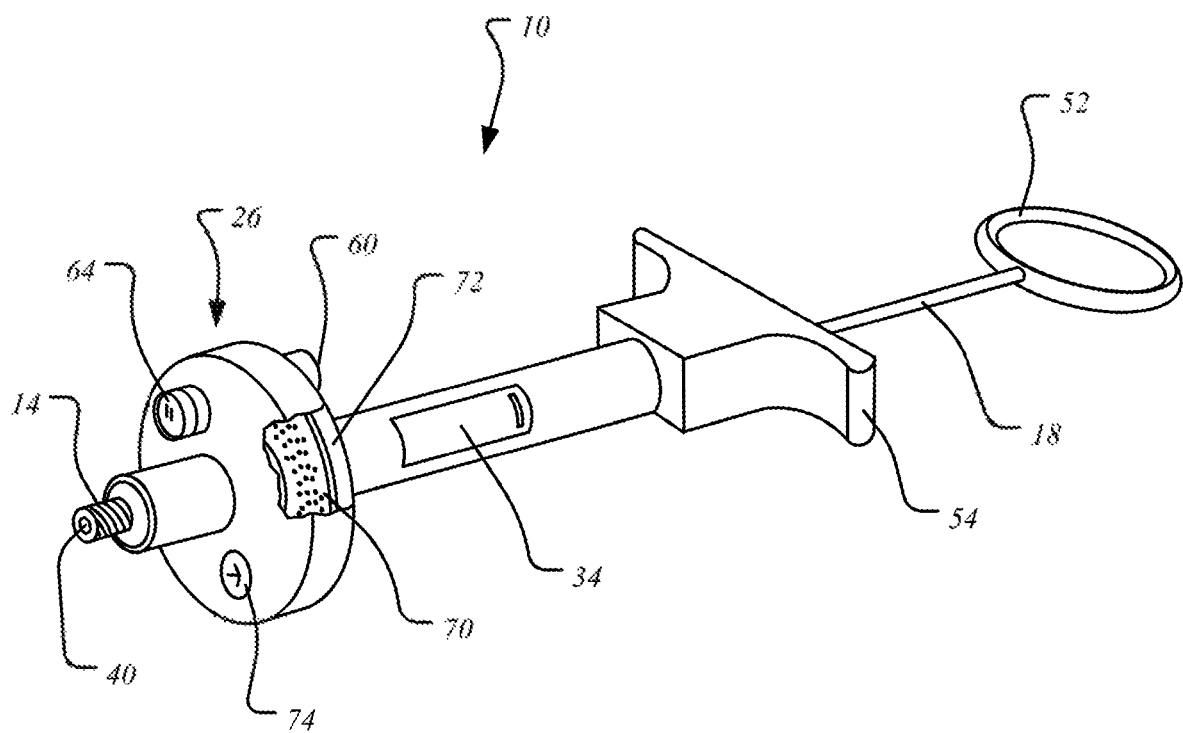
FIG. 2 is a perspective view of an anesthetic syringe having a Nipkow disk and transmitter.

In one embodiment, the hollow syringe barrel may completely enclose a drug cartridge, so that the cartridge is not viable or exposed to light from outside the syringe. In another embodiment, the exterior of the hollow syringe barrel may comprise one or more openings 32 to expose a portion of the drug cartridge. This may allow a user to visually verify blood in an aspirate, the identity of the drug cartridge, the engagement of the piston-engaging tip in the piston, and/or the position of the piston within the drug cartridge. In one embodiment, one or more openings on the exterior of the hollow syringe barrel may comprise removable or movable covers, such as a sliding cover 34. In another embodiment, an opening on the hollow syringe barrel may be covered with an optical filter so that a user can see inside the drug cartridge without certain ambient light wavelengths interfering with an optional spectrometer 36 taking a measurement within the cartridge. In one embodiment, an opening on the side of the hollow syringe barrel may allow a cartridge to be loaded through the side, and may or may not have a removable or movable cover. FIGS. 1B and 2 show anesthetic syringes with openings 32 and/or sliding covers 34.

In one embodiment, the first end of the barrel has a needle mount 14 extending outwards from the first end of the barrel 16. Preferably the end of the needle mount 14 is threaded to accommodate standard anesthetic syringe or dental needles. In an alternative embodiment, other types of needles, tubing, and/or cannulas may be useable with the syringe. In one embodiment, the needle mount is removably attached to the syringe barrel. Here, the needle mount may comprise a second screw thread 38 with the interior of first end of the barrel comprising a complementary thread. To assist in screwing the needle mount on and off, a part of the needle hole 40 may be hexagonal, showing a hex key to be inserted and used as a screw drive. In an alternative embodiment, the needle hole may comprise a different screw drive or the base of the needle mount may be shaped like a nut, configured to be removed and reattached with a wrench. Alternatively, the needle mount 14 may be removably attached by a different mechanism, such as a clamp, a pin, a bayonet mount, and/or other mechanisms.

In one embodiment, the outer diameter of the removably-attached needle mount at the connection to the first end of the barrel may be equal to the inner diameter of the hollow syringe barrel. In this embodiment, a drug cartridge may be loaded into the hollow syringe barrel when the needle mount 14 is removed, which may be possible with the syringes in FIGS. 1A, 1B, 2, and 4. In another embodiment, the side of the needle mount facing the interior of the hollow syringe barrel may have an annular stud. For a manual self-aspirating syringe, this stud may be configured to press against and deform the membrane or septum of a drug cartridge. By then decreasing pressure on the drug cartridge from the plunger end, the membrane becomes less deformed, which creates a negative pressure within the drug cartridge and causes a needle to aspirate into the drug cartridge. The annular stud may have an outer diameter of 1.5-4 mm, preferably 1.5-3 mm, more preferably 1.8-2 mm, an inside diameter of 0.4-3 mm, preferably 0.5-1 mm, more preferably 0.5-0.8 mm, and a height of 0.5-3 mm, preferably 0.6-2 mm, more preferably 0.6-1.8 mm. In an alternative embodiment, the first end of the barrel may have a fixed internal flange, which may or may not have an annular stud. In that alternative embodiment, the diameter of the needle mount at its connection to the barrel may be smaller than the interior diameter of the barrel, and a drug cartridge may be loaded from a side or from the second end of the syringe barrel. Alternatively, the needle mount may be fixed to the syringe barrel, and/or may be machined from the same piece of material.

In one embodiment, the interior of the syringe barrel 42 may be defined by a needle mount or inner flange at the first end and a bushing 44, or hollow cylindrical structure, spaced 50-100 mm, preferably 60-80 mm, more preferably 60-70 mm from the first end of the barrel. This bushing may be attached by a spring 46 to a second inner flange 48 near or at the second end of the syringe barrel. The bushing may be a hollow cylinder with an outer diameter slightly smaller than the inner diameter of the syringe barrel, so that the bushing may slide in the syringe barrel within the range of the spring. The inner diameter of the bushing may be slightly larger than the diameter of the plunger, so that the plunger can slidably and coaxially traverse the bushing and the interior of the syringe barrel. The bushing may also have a segment with a smaller outer diameter, in order to accommodate the spring around its circumference. The entire bushing may be contained in the syringe barrel, as in FIG. 1A, or the end distal the interior may extend outwards. In the embodiment where the bushing is contained, the bushing may have a length of 4-15 mm, preferably 6-12 mm, more preferably 8-12 mm. In the embodiment where the end of the bushing extends out of the syringe barrel, the bushing may have a length of 25-40 mm, preferably 27-37 mm, more preferably 30-35 mm, and may further have an annular flange at the distal end. Preferably the spring is a helical coil spring with a length of 3-13 mm, preferably 4-10 mm, more preferably 6-10 mm, and with an outer diameter of 6-12 mm, preferably 7-11 mm, more preferably 7-10 mm. The winding of the spring may be right or left handed, and the thickness of the wire may be 0.5-1 mm, preferably 0.5-0.9 mm, more preferably 0.5-0.8 mm. The spring may have a pitch of 0.1-4.3 mm, preferably 0.2-3.3 mm, more preferably 0.3-3 mm. Preferably, the spring and the bushing are configured to push a drug cartridge against the inner flange or needle mount in order to secure the drug cartridge within the interior of the syringe barrel, but without deforming the cartridge membrane or blocking the movement of the piston. In one embodiment, the bushing and/or spring are unattached, so that a bushing and/or a spring of a different length and/or compressibility may be exchanged to accommodate drug cartridges of different volumes. In another embodiment, rather than exchanging parts, a single spring and/or single bushing may be able to accommodate drug cartridges of different volumes. In another embodiment, a smaller or larger spring may be used, or more than one spring may be used. In another embodiment, the spring may be located on a different part of the bushing or outside of the bushing yet still provide a compressive force. In another embodiment, instead of a bushing, a washer, a hydraulic piston, a pneumatic piston, an elastomeric material, a compressible element, a sliding brace, some other hollow cylinder, or any combination may be used to secure the drug cartridge. However, in one embodiment, a moveable element may not be needed to hold the drug cartridge, and instead, the cartridge may fit securely between fixed ends of the interior syringe barrel.

As mentioned, the plunger 18 can slidably and coaxially traverse the bushing 44 and the interior of the syringe barrel 42, and in some embodiments, the bushing provides the primary support to coaxially position the plunger within the syringe barrel. In other embodiments, a washer, an annular flange, and/or a second bushing may provide support to the plunger. In another embodiment, the plunger may provide its own support, for instance, the plunger may comprise a segment with a larger diameter that slides within the barrel. In either embodiment, the plunger may slide against the inner surface of the supporting element, or may move on wheels, gears, bearings, and/or lubricant attached to the plunger and/or barrel. In some embodiments, the plunger may be supported and/or attached to a linear actuator mechanism, comprising gears, chains, screws, belts, or some other mechanical part, and in these embodiments the plunger may be rectangular or have a textured surface, such as gear teeth. The plunger may be able to slide and traverse the barrel interior completely from the needle mount 14 to a bushing 44, or the plunger may leave a gap of at least 5 mm, preferably at least 10 mm, more preferably at least 13 mm between the piston-engaging tip 22 and the inner side of the needle mount 50 or inner flange at the first end. The plunger may comprise a total length of 6-150 mm, preferably 7-130 mm, more preferably 90-120 mm. Except for the tip, the plunger may be cylindrical with a diameter of 2-6 mm, preferably 3-5.5 mm, more preferably 4-5.5 mm, or may be some other diameter or shape that allows it to slide freely while being supported within the syringe barrel. Preferably, a length 5-5.5 cm of the plunger adjacent to the piston-engaging tip has a diameter of 6 mm or smaller to allow the plunger to enter a standard drug cartridge as it moves the piston. In some embodiments, the plunger may be completely detached and removed from the hollow syringe barrel. In these embodiments, removing the plunger may allow a drug cartridge to be loaded into the hollow syringe barrel from the second end.

In one embodiment, the end of the plunger distal to the piston-engaging tip is attached to a thumb rest 52. Preferably this part of the plunger extends out and away from the second end of the barrel. In this embodiment, a finger grip 54 is attached to an exterior surface of the barrel adjacent to the second end. The thumb rest may be a ring with a circular or elliptical shape, as in a traditional aspirating syringe, and may have a smallest inner diameter of 15-35 mm, 20-30 mm, more preferably 20-25 mm. FIGS. 1A, 1B, and 2 show a thumb rest 52 that comprises a ring. Alternatively, the thumb rest may be a bar projecting from the end of the plunger and similar to the thumb rest or palm rest of a manual self-aspirating syringe. This may be in the form of a bar perpendicular to the plunger with the bar having a length of 20-70 mm, preferably 25-60 mm, more preferably 30-40 mm. In other embodiments, the end of the plunger may have a different shape, such as a disc, to accommodate a user's thumb or other finger, though in some embodiments the plunger may be configured for motorized movement and thus lack a form or a shape for manual control. A finger grip may be in the shape of a T with the stem centered on the central axis of the barrel and plunger. The inner corners of the T may be rounded to better fit a person's fingers. In one embodiment, a syringe with a thumb rest and a T-shaped finger grip may be held in one hand with an index finger and middle finger each in a corner of the T and curved around the cross-bar, with the thumb or palm of the hand on the thumb rest. Preferably the barrel, finger grip, and plunger may all be rotated relative to each other on the same central axis. In one embodiment, the finger grip may comprise two rings or two holes configured for the middle and index finger, or the finger grip may be present in some other form or shape. In the embodiment where the plunger is configured for motorized movement, the barrel may be configured to be held like a pencil, such as the syringes of FIGS. 3 and 4, and so a textured finger grip may exist on the exterior of the syringe barrel closer to the needle mount. This textured finger grip may be a portion or segments of ribs, ridges, grooves, knurls, bumps, or some other texture. Alternatively, the textured finger grip may be a cushion comprising an elastomeric compound such as silicone rubber, latex, butyl rubber, neoprene, and/or nitrile, and may be solid or comprise air pockets. The cushion may have a height or thickness of 1-4 mm, preferably 1.5-3 mm, more preferably 1.6-2 mm. In other embodiments where the plunger is configured for motorized movement, the external casing of the syringe may be shaped to be held like a power drill. In some embodiments, where the plunger does not have a thumb rest and is configured for motorized movement, the entire plunger may be contained by the syringe barrel and/or an external casing. In other embodiments, a motorized plunger may be housed in a smaller casing where the end of the plunger may protrude from the casing.

In the embodiment where the syringe may be configured for manual self-aspiration, the bushing at the second end of the barrel may be connected to an annular flange extending out of the barrel. This annular flange may be disposed between the finger grip and the thumb rest, or may be in some other arrangement or shape. The annular flange may have a greatest diameter or width of 8-20 mm, preferably 10-16 mm, more preferably 10-14 mm. Pressing on the annular flange may exert force on a drug cartridge and against an annular stud at the first end of the syringe barrel. This annular stud may deform a drug cartridge membrane, pushing the membrane inwards. Preferably this force on the annular flange or bushing may not influence the position or force on the plunger, as the plunger can freely slide while traversing the bushing. In other embodiments, instead of or in addition to an annular flange, a tab or a button may connect with the bushing and may be located off of the central axis of the syringe barrel and on either side of the finger grip. Sliding this tab or button may create a similar force on the bushing as the force created by pushing on an annular flange.

In one embodiment, the piston-engaging tip 22 of the plunger 18 may be the flat end of a cylinder or rod comprising the plunger. Alternatively, the piston-engaging tip may comprise a second cylinder 56 with a larger diameter and attached concentrically. The second cylinder may have a diameter of 0.2-2 mm, preferably 0.4-1.5 mm, more preferably 0.5-1.2 mm larger than the plunger, and may have a length of 0.5-5 mm, preferably 1-5 mm, more preferably 1-4 mm. In one embodiment, the diameter of the second cylinder does not exceed 6 mm so that it can enter a standard drug cartridge to move the piston. This cylinder may comprise the same material as the plunger or may comprise a different material or an elastomeric material, as listed previously. For a manual syringe configured for self-aspiration, the piston-engaging tip may consist solely of the second cylinder, or may simply be the end of the plunger. For a plunger 18 with a second cylinder 56, the second cylinder may prevent the plunger from being completely pulled out and separated from the syringe barrel. Where the syringe has a bushing 44, an inside diameter of the bushing may be smaller than the outer diameter of the second cylinder, to prevent the piston-engaging tip from being pulled completely through. Preferably, however, the second cylinder and the piston-engaging tip can be pulled completely inside a part of the bushing to allow clearance for a drug cartridge to be inserted from a side of the barrel. This may also pull the bushing against a spring 46 to create space for a drug cartridge.

In one embodiment, the piston-engaging tip 22 may comprise a harpoon 58 attached to the end of the second cylinder 56 and extending into the hollow syringe barrel. In the embodiment where there is no second cylinder, the harpoon may instead be attached to the end of the plunger. The harpoon 58 is a shape configured to pierce into and secure within the elastomeric piston of a drug cartridge, so that the plunger 18 is able to move the piston in either direction along the central axis of the syringe barrel. Preferably the harpoon or barb has a pointed tip at an end distal to the plunger. The harpoon may have a pointed shape attached by a shaft to the plunger or second cylinder. The shaft may have a length of 2-6 mm, preferably 2.5-5 mm, and a diameter 0.5-5 mm, preferably 0.5-4 mm, more preferably 0.7-3 mm. The pointed shape may be a cone, a pyramid, a spike, a fork, an arrowhead, or may be some other shape. FIG. 1B shows a harpoon 58 with a general cone shape. Preferably the base of the shape is a larger diameter than the shaft in order to resist extraction from a piston, and in some embodiments, the exterior of the pointed shape may comprise one or more barbs to securely engage within the piston. Preferably the piston-engaging tip, including a harpoon if present, does not exceed a diameter or largest width of 6 mm so that it may move within a standard drug cartridge.

In one embodiment, the anesthetic syringe has a nerve detector 26 attached to an exterior part of the barrel or to the illuminated indicator 24, and the nerve detector is configured to receive a radiative energy from a nerve. The nerve detector may be positioned 0.3-8 cm, preferably 0.4-4.5 cm, more preferably 0.5-2 cm from the first end of the barrel 16. In another embodiment, the nerve detector may not be attached to an exterior part of the barrel but may instead be connected to the first end of the barrel, such as the needle mount 14. The nerve detector may have a maximum height of 0.5-15 mm, preferably 0.7-10 mm, preferably 2-9 mm from the exterior surface of the syringe barrel or illuminated indicator. Preferably the nerve detector is configured to receive a radiative energy arriving from a source positioned away from the first end of the syringe barrel, and having a vector component parallel to a central axis of the syringe barrel. In other embodiments, the nerve detector may receive radiative energy within a conical field of view of 160° or less, preferably 120° or less. However, in some embodiments, a radiative energy from a location otherwise out of range may reach the nerve detector by scattering or reflection. In some embodiments, the nerve detector may not be fixed in position but may be slidably, rotatably, removably, or pivotally attached.

The radiative energy from a nerve may be non-ionizing electromagnetic radiation and comprise a wavelength or wavelengths in the ranges of 100 nm-400 nm (near ultraviolet), 400-700 nm (visible), 700 nm-10 μm (near infrared), 10 μm-100 μm (mid infrared), 100 μm-1 mm (far infrared), 1 mm-1 cm (extremely high frequency), 1 cm-10 cm (super high frequency), 10 cm-1 m (ultra high frequency), 1 m-10 m (very high frequency), 10 m-100 m (high frequency), 100 m-1 km (medium frequency), 1 km-10 km (low frequency), and/or 10 km-100 km (very low frequency). Preferably the non-ionizing electromagnetic radiation may comprise one or more wavelengths in the range 100 nm-10 m, more preferably 400 nm-1 m, or 1 μm-0.5 m. In some embodiments, longer wavelengths may be detected, such as 100 km-1 Mm (ultra low frequency), 1 Mm-10 Mm (super low frequency), and/or 10 Mm-100 Mm (extremely low frequency).

In other embodiments, the radiative energy may be ionizing electromagnetic radiation and comprise a wavelength or wavelengths in the ranges of 10 nm-100 nm (extreme ultraviolet), 100 pm-10 nm (soft X-rays), 10 pm-100 pm (hard X-rays), and/or 1 pm-10 pm (gamma rays). In one embodiment, the radiative energy may comprise both ionizing and non-ionizing radiation. In another embodiment, the nerve detector may be able to receive and distinguish radiative energy from two or more wavelengths, and in a further embodiment, the nerve detector may be able to receive the two or more wavelengths simultaneously. In another embodiment, the nerve detector, rather than detecting just a presence or absence of a radiative energy, is able to detect intensity changes of a sustained incoming radiation. In an alternative embodiment, the nerve detector may detect subatomic particles arriving from a nerve, for instance, electrons being deflected by a nerve.

In another embodiment, the radiative energy may be acoustic or sound waves, similar to sonography or ultrasonography. In another embodiment, the radiative energy may be an electric field, a magnetic field, or a gravitational field. In another embodiment, the nerve detector may locate a nerve by receiving radiative energy primarily from tissue that is not nervous tissue. In another related embodiment, the nerve detector may not receive radiative energy from a nerve itself, but from tissue adjacent or proximal to a nerve.

Preferably, the nerve detector comprises a detection circuitry to convert the radiative energy into a conductive electrical energy, and in one embodiment, the nerve detector comprises a photodetector 60 which functions as this detection circuitry. The photodetector may comprise one or more Si and/or InGaAs photodiodes, an avalanche photodiode, or a CCD, and may further comprise a filter, a prism, a beam splitter, and/or a diffraction grating to select certain wavelengths. In one embodiment, the photodetector may comprise a beam splitter to split the radiative energy into separate channels, each leading to a photodiode.

In one embodiment, the nerve detector may sense the change in electrical membrane potentials of nerve tissue caused by action potentials, as in the Neural Tissue Detector of US20150208934A1, although stimulation of the nerves may not be required. The change in electrical membrane potentials may cause the emission of electric fields and/or radiative energy. As other forms of tissue do not possess this degree of electrical activity, nerves are distinguished from other tissues.

In an alternative embodiment, the nerve detector may comprise one or more transmission lines, cables, waveguides, or optical fibers to channel the radiative energy to the detection circuitry. The detection circuitry may be attached to the syringe or located away from a patient.

Figure 4:
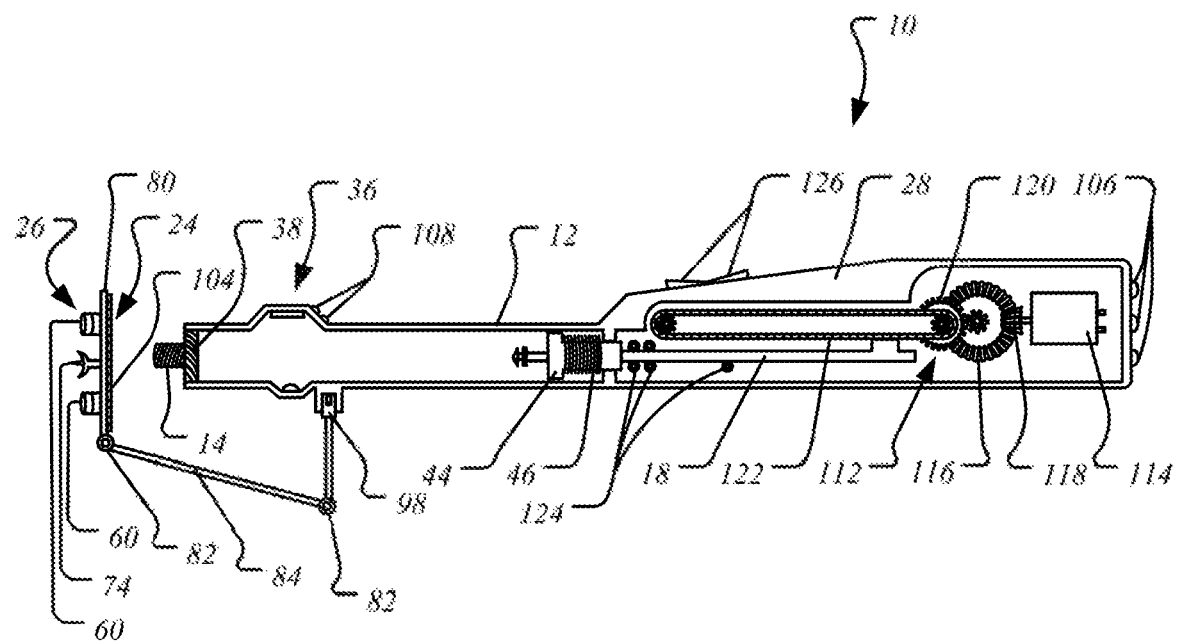
FIG. 4 is a side section view of an anesthetic syringe with an extended arm-mounted display panel and motor-driven plunger.

In one embodiment, the nerve detector 26 may comprise two or more photodetectors 60, and FIGS. 4 and 5B show embodiments of these syringes. These two or more photodetectors may be placed at the same distance from the first end of the syringe barrel. For instance, with a cylindrically-shaped barrel, two photodetectors may be placed diametrically opposed to one another, i.e. substantially across from each other, meaning with a spacing of 160°-200° between each other, where 180° would be directly across from each other. FIG. 5B shows two diametrically opposed photodetectors 60 on the syringe barrel. The photodetectors may be placed a distance from the first end as mentioned previously for the nerve detector. Three or more photodetectors may be placed substantially evenly around the barrel at a certain length, for instance, three photodetectors may be placed with 100°-140° between each other, and four photodetectors may be placed with 80°-100° between each other, all with the same distance from the first end of the syringe barrel. In another embodiment, six or more photodetectors may circumscribe the syringe barrel at a certain distance from the first end. In a further embodiment, the six or more photodetectors may form a ring around the syringe barrel. In another embodiment, the photodetectors may not be placed the same distance from the first end of the syringe barrel but may be staggered with distances from the first end that differ by 10 mm or less, preferably 5 mm or less. In one embodiment, where the exterior surface of the syringe barrel is not cylindrical, the photodetectors may instead be placed along a perimeter which encloses a plane perpendicular to a central axis of the syringe, or the photodetectors may be staggered 10 mm or less, preferably 5 mm or less from a certain perimeter.

In one embodiment, the nerve detector 26 may be able to distinguish a direction and/or intensity of radiative energy received. In one embodiment, the nerve detector 26 may comprise at least one focusing lens 62. A nerve detector having a focusing lens may have the focusing lens in the optical path between a collimating lens 64 and a detection circuitry, where the lenses and detection circuitry comprise an optical train. Preferably, in this embodiment, the detection circuitry comprises a photodetector. More than one lens may be used in the optical train, and the lenses may have a shape or lens type such as convex, concave, biconvex, biconcave, convex-concave, plano concave, plano convex, positive meniscus, negative meniscus, achromatic, apochromatic, cylindrical, gradient index, spherical, and/or some other shape. The focusing lens 62 may move towards or away from the detection circuitry or photodetector, in order to change the amount of radiative energy being directed. A focusing lens and/or other lenses may combine for a focal length of 10-50 mm, preferably 20-35 mm, and the lens diameters may be less than 5 mm, preferably less than 3 mm. The focusing lens may be attached by a threaded mount and may translate manually by a user rotating an exterior gear. Preferably, the nerve detector comprises circuitry that may automatically move the focusing lens and thus change the local plane of the nerve detector and/or the directions of collected radiation. This movement of the focusing lens may be controlled by a piezoelectric actuator, an ultrasonic motor, or some other linear actuator.

Figure 3:
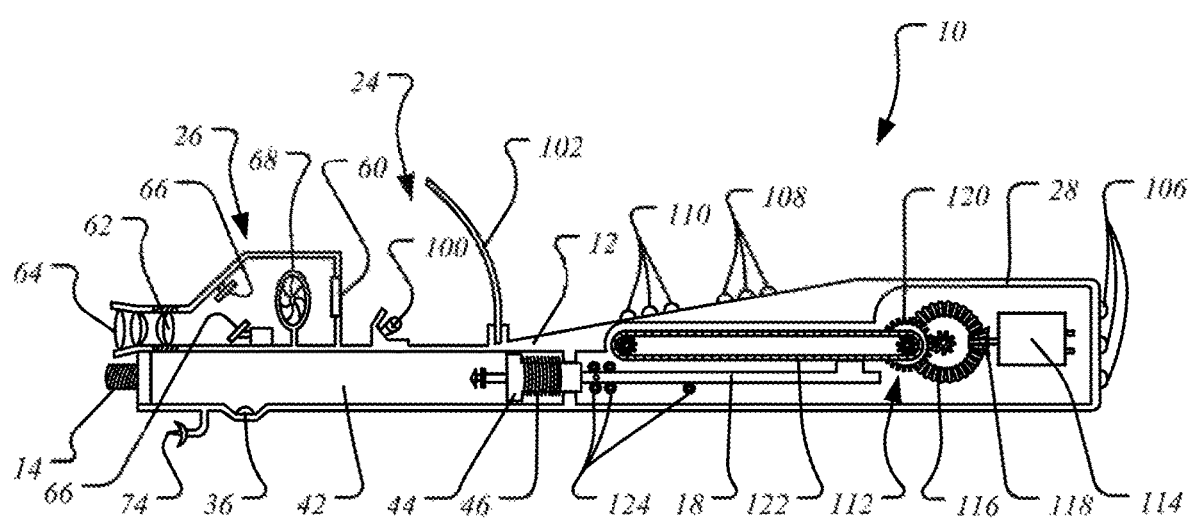
FIG. 3 is a side section view of an anesthetic syringe with a spectrometer, nerve detector, transmitter, and motor-driven plunger.

In one embodiment, the nerve detector may comprise at least one rotatable and/or pivotable reflector 66 configured to direct an incoming radiative energy. FIG. 3 shows a syringe with a nerve detector 26 having rotatable and pivotable reflectors 66. Depending on the direction of the incoming radiative energy, the reflector may direct the radiative energy towards or away from the detection circuitry or photodetector. The reflecting surface of the reflector may be flat or may have a concave or convex surface, such as an ellipsoidal or parabolic curve. The reflecting surface may be polished, such as a mirror or dichroic filter, or may be a diffraction grating. As mentioned, the reflector may be able to pivot, and this pivot may allow movement in one or more planes. Alternatively, the reflector may be able to rotate. For instance, the reflector may be a galvanometer mirror, which when rotated, allows the detection circuitry or photodetector to scan through different angles of incoming radiation. The rotation speed may be 600-10,000 rpm, preferably 800-5000 rpm, or 800-1,000 rpm. In one embodiment, two or more galvanometer mirrors may be used with a single detection circuitry or photodetector to allow scanning in more than one plane of incoming radiation. One or more reflectors, including mirrors, may have diameters of 0.1-5 mm, preferably 0.2-4 mm. In one embodiment, arrays of reflectors may be used, similar to mirrors used in a digital micromirror device, and each reflector may have smaller dimensions, such as widths or diameters of 5-100 μm, preferably 5-20 μm, and be able to pivot independently of the other reflectors.

In a related embodiment, the nerve detector 26 may further comprise an adjustable pinhole 68. This adjustable pinhole may also be known as an iris, a stop, or diaphragm, and further allows control over which directions of incoming radiation are detected by the detection circuitry or photodetector. The adjustable pinhole may form an aperture diaphragm or a field diaphragm, and may or may not be in positioned in a conjugate image plane. In some embodiments, a rectangular or oval slit may be used instead of a round pinhole. Preferably the adjustable pinhole sits in a frame that is the same size or smaller than a lens or lenses of the nerve detector, and the adjustable pinhole may be able to open to diameters of 1-95%, preferably 2-80% of the frame's inner diameter. In some embodiments, the pinhole opening may be adjusted to a diameter of 0.5-100 μm during imaging, though in other cases, the pinhole may be opened to diameters larger than 100 μm during imaging. The pinhole frame may also be moveable towards or away from the detection circuitry or photodetector. In one embodiment, the nerve detector 26 comprises both an adjustable pinhole 68 and a rotatable and/or pivotable reflector 66, as in FIG. 3, and this combination allows the nerve detector to scan through different directions of incoming radiation in a manner similar to a confocal microscope. The nerve detector may then be able to distinguish a depth of a source of an incoming radiation, for instance, the depth of a nerve in a patient's tissue. In one embodiment, the combination of adjustable pinhole and rotatable and/or pivotable reflector may be able to construct a 2D or 3D image from incoming radiation. Preferably the adjustable pinhole and rotatable and/or pivotable reflector are controlled automatically by a computing device.

In a related embodiment, the nerve detector may comprise a Nipkow disk 70 rotatably attached to and encircling the syringe barrel 12. The Nipkow disk 70 comprises a plurality of pinholes, and preferably the Nipkow disk is housed in a casing 72, as shown in FIG. 2. The pinholes of the disk may be configured to direct rays of an incoming radiative energy to at least one photodetector 60. The Nipkow disk may have an outer diameter of 1.5-5.5 cm, preferably 2-4 cm, more preferably 2-3 cm, and an inner diameter of 1-3 cm, preferably 1.5-2.5 cm, more preferably 1.5-2 cm. The Nipkow disk may comprise 50-2,000 pinholes, preferably 100-1,500 pinholes, more preferably 100-1,000 pinhole. However, in one embodiment, the Nipkow disk from a spinning disk confocal microscope may be used and may comprise more than 2,000 pinholes. The pinholes may have diameters of 10-100 µm, preferably 20-80 µm, more preferably 30-60 µm, and may be arranged along nested spirals, along radii from the disk center, along concentric circles, or may be in some other arrangement. The Nipkow disk may have a thickness of 0.3-1 mm, preferably 0.4-0.9 mm, more preferably 0.5-0.8 mm. In one embodiment, radiative energy is received through one or more pinholes and is detected by a CCD. In this configuration, rotation of the Nipkow disk allows the nerve detector to scan the pinholes through a window of incoming radiative energy. One rotation of the disk may scan the pinholes through the image at least once, preferably at least four times, though some designs of Nipkow disks may scan through the image at least eight times in one rotation. The detected radiative energy from the scanning pinholes may be used to construct a 2D image, or combined with focal planes at different depths to construct a 3D image. The Nipkow disk may be rotated at a rotational speed of 100-3600 rpm, preferably 600-2000 rpm, more preferably 800-2000 rpm, and this rotating disk may provide a gyroscopic stability to help steady the anesthetic syringe against sudden movements. In one embodiment, more than one photodetector and/or CCD may be positioned around a circumference of the syringe barrel. The Nipkow disk may be rotated by an electric motor with a gear coupling to the inner or outer diameter of the disk. Alternatively, the Nipkow disk may be rotated by compressed air delivered by pneumatic tubing, similar to the rotation mechanism used in a dental drill or other pneumatic drill.

In another embodiment, a second Nipkow disk may be rotationally coupled to the first disk and encircle a part of the syringe barrel between the needle mount and the first Nipkow disk. This second Nipkow disk may have the same bulk dimensions, but rather than pinholes, the second Nipkow disk may comprise a plurality of microlenses with each aligned in the optical path of one pinhole of the first disk. Preferably the microlenses have diameters of 2-5 times greater than the pinholes on the Nipkow disk. These microlenses enable a greater amount of incoming radiative energy to be directed through the pinholes and to one or more photodetectors or CCD of the nerve detector.

In an alternative embodiment, the Nipkow disk may instead be housed in a casing attached to an arm extending past the needle mount. In this alternative embodiment the Nipkow disk may instead encircle a needle attached to the needle mount, allowing the disk to have a smaller inner diameter. To facilitate mounting and removing the needle, the casing may be removably attached to the syringe barrel or to the arm. In another alternative embodiment, the Nipkow disk may not encircle a central axis of the syringe barrel, and may instead be positioned with its largest fact parallel to a central axis of the syringe. In this arrangement, incoming radiation may be collected by a prism, reflector, optical fiber, or some other device and directed to the Nipkow disk. In a related alternative embodiment, the Nipkow disk and detector may be housed separately from the syringe barrel but attached to a cable or optical fiber that may channel the radiative energy to the disk and detector.

Alternatively, 2D or 3D images from incoming radiation may be acquired without a rotatable and/or pivotable reflector or Nipkow disk but with detection circuitry that allows and distinguishes more than one direction of incoming radiative energy. For example, the exterior of the syringe barrel may have more than one photodetector, and these separate photodetectors may be able to combine information on the direction of incoming radiation in order to determine the depth or distance of a radiation source, or to construct a 2D or 3D image. FIGS. 4 and 5B show syringes that each have a nerve detector 26 comprising two photodetectors 60.

In an alternative embodiment, the nerve detector may be able to determine other parameters of a tissue, such as temperature, composition of water, fat, or protein, electrical activity by action potentials, and/or tissue density. The anesthetic syringe may thus be useable for taking vital signs, determining potential tumor sites by tissue density, and/or in guiding surgical operations by distinguishing different types of tissues. In another alternative embodiment, the anesthetic syringe may comprise a pen or marking element, allowing a user to mark the location of a nerve and/or an ideal injection location on a patient's tissue. This may be done prior to attaching a needle to the syringe, or may be used to plan a location of a surgical incision. Alternatively, a marking element could be attached to the syringe needle, or to the shield of the syringe needle.

In one embodiment, the anesthetic syringe 10 has a transmitter 74 configured to emit a radiative energy onto the nerve. This emitted radiative energy may be any of those mentioned previously as receivable radiative energy, including ionizing and non-ionizing electromagnetic radiation, sound energy, electric fields, magnetic fields, and/or gravitational fields. The transmitter may be able to emit one wavelength, though preferably it may emit more than one wavelength or a range of wavelengths. In one embodiment, the transmitter may emit radiative energy in separate ranges of wavelengths, for example, a transmitter may be able to emit infrared and UV light. The transmitter may only be able to emit one wavelength or type of radiative energy at a time, though in other embodiments, the transmitter may be able to simultaneously emit more than one type of wavelength. In another related embodiment, the transmitter may be able to continually scan through frequencies or modulate the power, phase, polarization, or direction of the radiative energy. In an alternative embodiment, the transmitter may emit particles, such as electrons, rather than radiative energy.

In one embodiment, the transmitter may emit coherent radiative energy, such as in the form of a laser. In another embodiment, emitted radiative energy may be unidirectional. The transmitter may comprise a curved reflector, such as a parabolic reflector, to collimate and direct the emitted radiative energy. For example, FIGS. 2, 3, and 4 show transmitters 74 having curved reflectors. In another embodiment, a syringe may use two or more transmitters to emit energy to a point from more than one angle. For example, FIG. 5D shows a syringe barrel 12 with two transmitters 74 mounted on opposite sides. In some embodiments, a transmitter may not be fixed in position but may be slidably, rotatably, removably, or pivotally attached.

In one embodiment, similar to the nerve detector, the transmitter may use lenses, pinholes, rotatable/pivotable mirrors, an interferometer, or other optics to manipulate the direction of emitted radiative energy. In this manner, a transmitter may be able to scan or direct emitted radiative energy across a line, area, or within a volume of a tissue. In a related embodiment, a transmitter and nerve detector may share certain optics. For instance, an emitted radiative energy may be directed from a mirror and focused through a lens, and an incoming radiative energy may arrive through the same lens and be directed by the same mirror. In this case where the transmitter and nerve detector share one or more optics, preferably the syringe has a beam splitter, dichroic mirror, diffraction grating, prism, optical filter, acousto-optic tunable filter (AOTF) and/or some other optical device to separate and/or direct the transmitted radiative energy and received radiative energy to different directions.

In one embodiment, the transmitter or nerve detector may modulate properties of the emitted or received radiative energy, such as by changing or controlling polarization, phase, pulse width, exposure time, and/or other parameters. In a related embodiment, a transmitter and nerve detector used in tandem may be able to detect different types of tissues by comparing one or more of these physical properties between emitted and received radiative energy. These changes may arise from fluorescence, absorption, phosphorescence, autofluorescence, and/or other interactions between the emitted radiative energy and the irradiated tissue. In another embodiment, the radiative energy from the transmitter may be reflected back to the detector by a type of tissue. By detecting the reflected radiative energy, the detection method may be similar to radar. In a further embodiment, the detection method is a radar system similar to ultrawideband radar, which uses pulsed or frequency-modulated radar over the frequency range of 1-100 GHz. In other embodiments, biological activity such as changes in neuron membrane potentials may generate or change emitted radiative energy, which is then detected.

In one embodiment, a pharmaceutical compound may be administered topically, orally, or intravenously to a patient. This pharmaceutical compound may cause a release of a radiative energy from a nerve or from tissue adjacent to a nerve, and this radiative energy may be detected by the nerve detector. In a related embodiment, this pharmaceutical compound may not release radiative energy unless stimulated. For example, a pharmaceutical compound comprising a conjugated fluorophore may target and/or bind to a nerve tissue. The fluorophore may be excited by an emitted light from a transmitter on the syringe, or a transmitter separate from the syringe may be used as an excitation light. The excited fluorophore may then emit a radiative energy that is received by the nerve detector. The fluorophore may be fluorescein isothiocyanate, coumarin, Texas-Red, anthracene, Alexa Fluor 350, 405, 430, 488, 500, 514, 532, 546, 555, 568, 594, 610, 633, 635, 647, 660, 680, 700, 750, or 790, BODIPY, DAPI, NBD, Cy2, Cy3, Cy3B, Cy3.5, Cy5, Cy5.5, Cy7, TRITC, a fluorescent protein, or some other fluorophore. In other embodiments, a phosphorescent compound may be used in place of a fluorophore. The pharmaceutical compound may targeting binding to part of the nerve fiber, such as to neurofilament protein, myelin, Schwann or other neuroglia cells, and/or other neuron-specific proteins. The pharmaceutical compound may be a small molecule drug, a biofunctionalized nanoparticle, an antibody drug conjugate, or some other compound. In a related embodiment, a capsule or solid device may be implanted or held in contact with a tissue of a patient. The capsule or solid device, when stimulated, may cause a release of radiative energy from a nerve.

In one embodiment, an external energy source not attached to the syringe may be used to cause a nerve in a tissue to emit a radiative energy. This exterior energy source may use a non-radiative energy, for example, direct electrical stimulation of a patient's tissue. Electrical stimulation may be performed by contacting a patient's tissue with one or more electrodes, and in one embodiment, a syringe needle may function as an electrode. In other embodiments, an exterior energy source may use a radiative energy, such as an ultrasound probe, an X-ray tube, a microwave generator, a laser, or a gas discharge tube, and the device providing the energy may or may not physically contact the patient.

The transmitter may be located next to nerve detector and/or photodetector, such as within 15 mm or less, preferably 10 mm or less. FIG. 4 shows an anesthetic syringe with the transmitter 74 located near and between two photodetectors 60. In another embodiment, the nerve detector and transmitter may be located on opposite sides of the syringe barrel, for instance, in FIGS. 2 and 3. However, in other embodiments, the transmitter may be located on a part of the syringe farther away, having a distance of 3-10 cm, preferably 4-8 cm from the nerve detector.

In one embodiment, a syringe with a nerve detector and transmitter may be able to defect nerves by the contrast of reflection and/or adsorption of an emitted radiative energy, similar to existing subcutaneous blood vessel viewers, such as the VeinViewer and vascular/vein pattern recognition technologies. Here, the transmitter may emit an infrared light.

However, in one embodiment, the anesthetic syringe does not have a transmitter. In one embodiment, the radiative energy is detected without radiative stimulation or other stimulation from the anesthetic syringe. FIGS. 1A, 1B, 5A, and 5B show anesthetic syringes or syringe barrels without transmitters. In a related embodiment, an anesthetic syringe with a transmitter may be able to detect radiative energy from a tissue and/or a nerve without the syringe having to emit radiative energy. For instance, the transmitter may be shielded by a shutter or a cover, or turned off, while the nerve detector receives radiative energy. Alternatively, an external transmitter, as mentioned previously, may be used with a syringe that does not have a transmitter.

As mentioned previously, the anesthetic syringe 10 has an illuminated indicator 24 electrically connected to the nerve detector 26. This illuminated indicator is configured to receive a signal from the nerve detector and then indicate at least one direction to move the anesthetic syringe to deliver an anesthetic injection proximal to a nerve. The illuminated indicator may comprise at least one indicator light 76, though preferably it may comprise at least four indicator lights. The indicator lights may comprise one or more LEDs, organic light-emitting diodes (OLEDs), active-matrix organic light-emitting diodes (AMOLEDs), backlighted liquid crystal display (LCD), backlighted E-ink, quantum dots, incandescent bulbs, cathode ray tubes, lasers, plasma cells, and/or gas discharge lamps. The indicator lights may have a circular form or rectangular form with no particular indicating direction, or the indicator lights may be in the shape of arrows, triangles, angles, carets, or some other shape to convey a direction. For example, FIG. 5B shows round indicator lights 76 that show no direction by themselves but instead indicate a labeled direction 78 on the syringe barrel. As another example, FIG. 5A shows an illuminated indicator having lights 78 in the shape of arrows. In another embodiment, several indicator lights may form a numeric or alphanumeric display, or may form an array of pixels. In an alternative embodiment, one or more indicators may be used that are not illuminated, for example, an LCD or E ink display that is not backlighted, or a mechanical display device.

In one embodiment, the illuminated indicator comprises indicator lights that indicate whether to move the syringe or an attached needle along a direction on one of two perpendicular axes. In a further embodiment, the indicator lights may indicate to move up, down, left, or right. When movement in a certain direction is achieved, the corresponding indicator light may change color or turn off. When a desired position is reached, all the indicator lights may blink in a certain sequence or change color. Alternatively, a different light could indicate that a desired position is achieved, and/or to what degree of certainty. Different positions may be indicated by vector addition of the different distances, for instance, moving the syringe to a position on a diagonal may be indicated by two perpendicular directions being indicated, for instance, "up" and "right." In a further embodiment, direction-indicating lights may show a relative distance to move the syringe. For instance, a double arrow to the left may show that more movement to the left is required than just a single arrow to the left. Alternatively, relative distances could be indicated by blinking, by light intensity, by light color, or by displaying a number. In FIG. 5B, the number of illuminated lights 76 corresponding to a particular direction may relate to the distance to move the syringe in that direction. In an alternative embodiment, the anesthetic syringe may comprise a speaker 622 or buzzer to indicate a direction to move the syringe or if a desired position is reached. In another embodiment, the illuminated indicator may display or signal other information, such as the identity of a drug, the injection flowrate, the injection pressure, the injection volume, the presence of an aspirate, the presence of blood in an aspirate, the patient's identity, the capacity of a battery, the status of a spectrometer, values of biomarkers such as hemoglobin concentration, wireless connectivity, and/or other parameters. In one embodiment, the anesthetic syringe may further comprise a digital storage medium 604 to record the information presented on the illuminated indicator, or to store other information. The illuminated indicator may display numbers or letters with a segmented display (such as a 7-segment, 9-segment, 14-segment, or 16-segment display), a dot matrix display, or may indicate information by illuminating a light next to a label or a label itself on the syringe, similar to what has been mentioned with FIG. 5B. In one embodiment, the illuminated indicator may further comprise a touch screen, which may be used by a medical professional to change parameters of the syringe or to view different information. In related embodiments, the illuminated indicator may comprise buttons or switches for the same purpose.

Figure 5E:
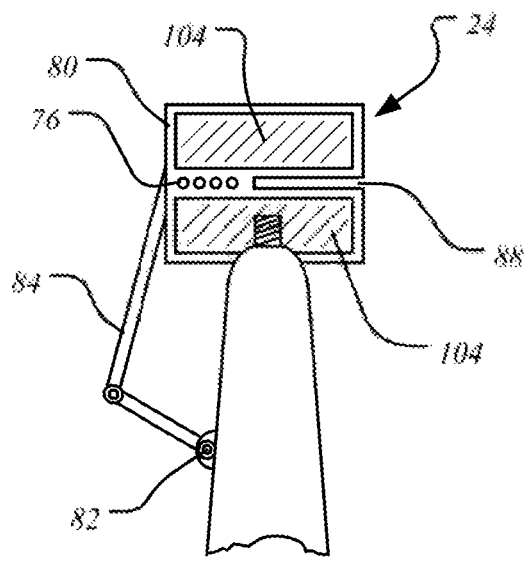
FIG. 5E is a portion of an anesthetic syringe with a hingedly attached, arm-mounted display panel having a slot to accommodate a needle.

In one embodiment the illuminated indicator may comprise a display panel 80, though in other embodiments the illuminated indicator may comprise more than one display panel attached at different locations on the syringe barrel. FIGS. 1A, 1B, 4, 5A, and 5C-5F show syringe barrels with display panels. A display panel may have a longest dimension of 0.2-5 cm, preferably 0.5-3.5 cm, more preferably 1-3 cm, and a shortest dimension of 0.1-4 cm, preferably 0.4-3 cm, more preferably 0.5-2.5 cm. The display panel may have a thickness of 0.5-7 mm, preferably 0.6-5 mm, more preferably 0.8-4 mm, and in some embodiments the thickness may vary at different parts of the display panel. A smallest display panel may comprise one indicator light. The display panel may have a rectangular shape or a curved shape, such as a semicircle attached to and encircling a part of the syringe barrel circumference. In some embodiments, a display panel may curve with concavity along the central axis of the syringe. Preferably the display panel is substantially perpendicular to the exterior surface of the syringe barrel, where "substantially perpendicular" refers to an angle of 75°-105°, preferably 80°-100°, where 90° describes a perpendicular angle. Preferably at least one side of the display panel is planar or curved and faces in the direction of the second end of the syringe barrel. However, in other embodiments, a display panel may be tilted at different angles, moveable by a hinge, and/or slidable on a track. FIGS. 5C and 5D show a display panel 80 attached to the syringe barrel 12 by a hinge 82. A display panel attached by a hinge or pivot may be turned, folded down, or collapsed against the syringe barrel. FIG. 5D shows the display panel 80 folded down against the syringe barrel 12. In some embodiments, the syringe may comprise more than one display panel. For example, where four indicator lights are used to indicate moving the syringe in at least one of four directions, those four indicator lights may each be attached to a separate display panel and attached at four locations around a circumference or perimeter of the syringe barrel. Alternatively, three display panels may be spaced with 89°-91° between them on a circumference of the syringe barrel, with each display panel having at least one indicator light, with the middle display panel having two indicator lights. In another version, the two display panels having only one indicator light each could be placed at angles less than 90°, or may be combined as one display panel as in FIG. 5A. In one embodiment, the illuminated indicator may not have a display panel, and instead the indicating lights may be directly attached to the exterior surface of the syringe barrel. In a further embodiment, the lights may be flush with or recessed within the exterior surface of the syringe barrel.

In an alternative embodiment, the needle may be offset at an angle from the central axis of the syringe barrel, for example 130°-170°, preferably 135°-160°, more preferably 140°-150°. Alternatively, a syringe may be constructed with a hinge in order to move to such an angle. This may allow the needle end of a syringe to take up less space by having an illuminated indicator display panel placed at the inside of the angle. This change in shape may be helpful for a medical professional performing an oral anesthetic injection or some other injection where space is limited.

In one embodiment, the illuminated indicator may be hingedly or slidably attached to the exterior of the syringe. In this embodiment, a medical professional may use the illuminated indicator to locate a nerve, and then he or she may tilt, collapse, fold down, or move the illuminated indicator out of the way so as not to interfere with the injection procedure. In one embodiment, the illuminated indicator may be removably attached to the syringe for the same purpose.

In another embodiment, the illuminated indicator may be attached to the syringe barrel by an extended arm 84. The arm may be attached to an exterior side of the barrel at a location of 0.3-8 cm, preferably 0.4-4.5 cm, more preferably 0.5-2 cm from the first end of the barrel. The arm may extend from the barrel surface by 0.3-1.5 cm, preferably 0.4-1.2 cm, more preferably 0.5-1.0 cm, and then extend towards and beyond the needle mount 14. The length of the arm may be 1-13 cm, preferably 2-10 cm, more preferably 3-8 cm. The arm may comprise material as listed previously for the syringe barrel, and may further comprise an electrical wiring to connect the illuminated indicator with the nerve detector and/or other electronic parts. This electrical wiring may be wound or attached to the exterior of the arm or may be threaded through the interior of the arm.

Figure 5F:
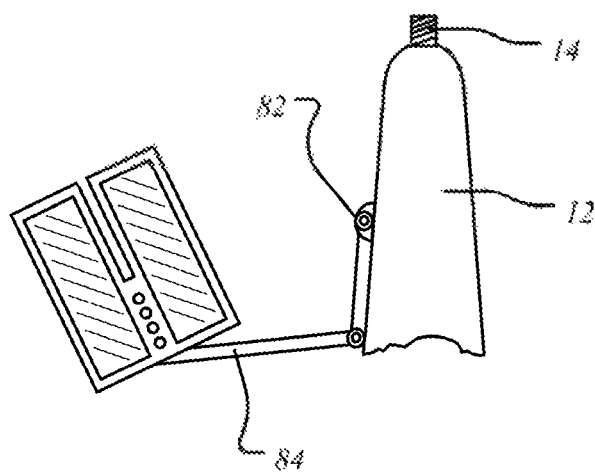
FIG. 5F is the anesthetic syringe in FIG. 5E with the arm-mounted display panel turned to an open position.
Figure 5G:
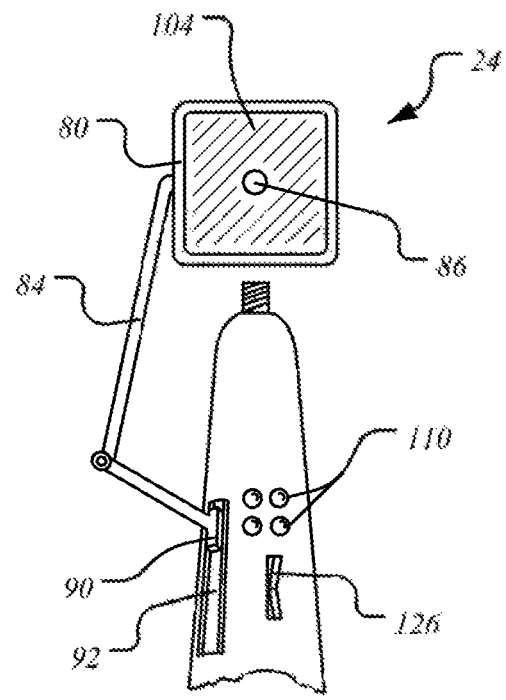
FIG. 5G is a portion of an anesthetic syringe having a slidably attached, arm-mounted display panel.

In one embodiment, the illuminated indicator comprises a first display panel mounted to an arm attached to the barrel. FIGS. 4, and 5E-5H show the illuminated indicator 24 and display panel 80 being attached to the syringe barrel 12 by an arm 84. In a further embodiment, the first display panel 80 is positioned outwards from the first end of the barrel 16 and shaped to accommodate a needle attached and extending outwards from the needle mount 14. Here, a display panel may be mounted to the end of the extended arm and may be adjacent to a needle attached to the needle mount. The dimensions of the arm may be of those described previously. In this case, the smallest distance from the needle to the edge of the display panel may be less than 10 mm, preferably less than 8 mm, more preferably less than 6 mm. In a further embodiment, the needle may traverse the display panel through a hole 86 having a diameter of 1.5-10 mm, preferably 2-8 mm, more preferably 2-6 mm. In this configuration, the forward position of the display panel allows a medical professional to clearly see information from the illuminated indicator as he or she finds an injection location. This may allow the positioning of the syringe with greater accuracy. In other embodiments, a single display panel may be attached to the syringe barrel by two or more arms. In another embodiment, the needle may pierce through the display panel, for example, though a rubber septum built into the display panel. In this configuration, the needle may provide some support to a display panel and reduce its vibrations. In one embodiment, the arm and the display panel may be fixed and immovable. Preferably, though, one or more segments of the arm or display panel may comprise one or more hinges and/or pivots in order to fold or move the display panel to a different position. For example, FIGS. 5E and 5F show the arm 84 attached to the syringe barrel 12 through a hinge 82, illustrating a closed configuration and an open configuration, respectively. Here, the display panel 80 is designed with a slot 88 to accommodate an attached needle. A pivot or binge may comprise an electrical connection in order to electrically connect the illuminated indicator with the nerve detector. Alternatively, electrical wiring from the arm may have a flexible, unattached length of wiring to allow the arm to move freely. In some embodiments, the arm may collapse or fold down against the syringe barrel. In another embodiment the arm may be slidably attached to an exterior side of the syringe barrel, and thus may move parallel to a central axis of the syringe barrel. In this configuration the end of the arm 90 slidably attached to the syringe barrel may fit into a sliding track 92, as shown in FIG. 5G. Having the arm-mounted display panel slidably attached to the syringe barrel may allow an attached needle to traverse the display panel through a hole 86 or through an embedded seal, membrane, or rubber septum. The display panel may slide towards the syringe barrel before or during the insertion of the needle into a tissue. In another embodiment, an arm-mounted display panel may be slidably attached to the syringe barrel but positioned to the side of an attached needle. The sliding track may comprise one or more linear electrodes to form and maintain electrical connections with the arm as if slides. Alternatively, electrical wiring from the arm may have a flexible, unattached length of wiring to allow the arm to slide freely. The track may have a length of 1-9 cm, preferably 2-8 cm, more preferably 3-6 cm, and the arm may move manually in the track or by a motor. In a related embodiment, with a slidably attached arm-mounted display panel, the hole 86 may be equal to or larger than the outer diameter of the syringe barrel, enabling the first end of the syringe barrel to traverse the display panel. In a related embodiment, rather than the arm being attached to a sliding track on the barrel, the arm itself may be extendable to different lengths, using, for example, a telescoping structure.

In one embodiment, the nerve detector and/or the transmitter are attached to the illuminated indicator. In these embodiments, preferably the illuminated indicator comprises a display panel, with or without an arm. In these cases, the nerve detector and/or transmitter may be placed in a less obstructed location on the syringe, allowing wider angles of received and/or transmitted radiative energy. In addition, the nerve detector and/or transmitter may be placed further from the needle mount, which locates the nerve detector and/or transmitter closer to the tissue. This may allow more accurate nerve detection. FIG. 4 shows an example of an arm-mounted display panel 80 having a transmitter 74 and nerve detector 26 attached and facing away from the syringe barrel. The nerve detector 26 comprises two photodetectors 60 on each side of the transmitter 74. In a related embodiment, where a syringe comprises a Nipkow disk, the transmitter 74 may be attached to an exterior side of the Nipkow disk casing 72, as in FIG. 2.

In one embodiment, the arm may be removably attached to the display panel and/or the syringe barrel. Similar to the previously-mentioned embodiments, a medical professional may use the illuminated indicator to find an injection site and then remove the display panel, or both display panel and arm, from the syringe prior to making an injection. The removable attachment mechanism may be one that simultaneously provides an electrical connection, such as a head phone jack, a Mini-USB, a Micro-USB or some other plug and socket connector. FIG. 4 shows a Micro-USB connection 98 between the arm 84 and the syringe barrel 12. Alternatively, the removable attachment mechanism may comprise an electrical connection and a second connection providing structural support. The second connection may through be a key find keyhole mechanism, a pair of magnets, a threaded connector, a bayonet mount, a clutch, a latch, a tongue and groove joint, a snap fastener, an R-clip, a clamp, or some other structure.

Figure 5H:
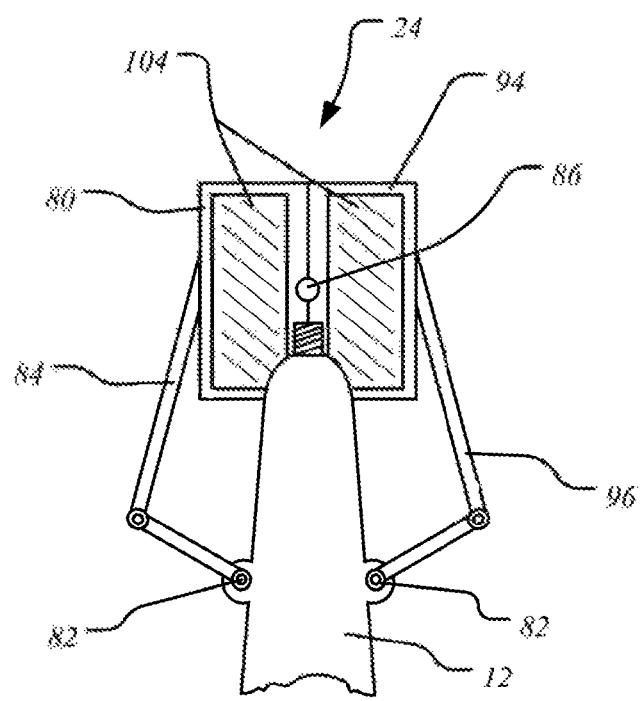
FIG. 5H is a portion of an anesthetic syringe having two hingedly attached, arm-mounted display panels on separate arms.

In another embodiment, where the illuminated indicator 24 comprises a first display panel 80 mounted to an arm 84 attached to the barrel, the illuminated indicator further comprises a second display panel 94 mounted to a second arm 96 attached to the barrel. The second display panel and second arm may be any of those described previously, and may be similar or different to the first display panel and arm. In one embodiment, the two arms may pivot towards each other on opposite sides of an attached needle. In a further embodiment, the two display panels may touch or connect with one another, and form an open shape or hole 86 to accommodate an attached needle. This hole may be similar to that described earlier for a needle traversing the first display panel. For example, FIG. 5H shows a syringe barrel 12 with a first display panel 80 and second display panel 94 in this configuration. The first display panel and the second display panel are able to pivot towards and away from each other. In one embodiment, the illuminated indicator may comprise an arm but not have a display panel. Instead, a portion of the arm may comprise indicator lights in order to display them in view of an attached needle. In another embodiment, two or more display panels may be mounted to a single arm.

In one embodiment, the illuminated indicator may comprise a projector to project light and/or an image onto a surface. For instance, the illuminated indicator may project a light onto an exterior surface of a tissue to show a location of a nerve. In another embodiment, the illuminated indicator may project light onto an opaque or semitransparent display panel attached to an external part of the syringe barrel with or without an arm. The illuminated indicator 24 of FIG. 3 shows this configuration where a projector 100 forms an image on the curved semitransparent display panel 102, which is removably attached to the syringe barrel 12. This arrangement may instead be located on a syringe where a medical professional may see the patient's tissue through the display panel, but with an overlay of one or more projected lights or images, similar to a heads-up display (HUD). In a related, though alternative embodiment, an illuminated indicator may not be attached to the syringe and may instead form a projection on a medical professional's safety glasses, or may comprise an external screen, such as a computer monitor. In another embodiment, the illuminated indicator may form a 3D image by stereoscopy, autostereoscopy, or multiscopy.

Where the illuminated indicator has a display panel mounted to an arm attached to the barrel, the display panel may comprise indicator lights as mentioned previously. A plurality of these lights may together form image pixels. In one embodiment, the illuminated indicator comprises a first LED display 104 mounted to an arm attached to the barrel. In a further embodiment, this first LED display comprises at least 625 LEDs. Here, the at least 625 LEDs may be arranged in a 25×25 array or more and may be configured as pixels to form an image. FIG. 5C shows an alternative embodiment, where a display panel with an LED display 104 is directly attached to the syringe barrel without an arm. Preferably the LED display comprises at least 1,000 LEDs, more preferably at least 5,000 LEDs. In one embodiment, the LED display may be similar to a modern computer LED monitor screen, tablet screen, and/or smartphone screen and may produce at least 100 pixels per square inch (PPI), preferably at least 200 PPI, more preferably at least 300 PPI. In alternative embodiments, an image may be formed with less than 625 LEDs and/or less than 100 PPI. The image formed may be monochromatic, or multicolored LEDs may be used to produce images of more than one color. The LEDs may be configured to emit light at only one power intensity, or they may be configured to emit light at more than one intensity. In one preferred embodiment, the image formed by the LED display shows a nerve location in real time, for instance, by representing an outline of a nerve or the center of a nerve on the display. This imaging may be considered a type of tomography. In other instances, the image formed may represent an image or images of other tissues, for example, epithelial tissue, bone tissue, blood vessels, or other tissues. The LED display may form an image with minimal image processing based on intensities or other characteristics of the radiative energy received by the nerve detector. In other cases, the nerve detector may combine information from two or more properties of the radiative energy and compute an image of a nerve or other tissue. In other embodiments, the nerve detector may be able to interpret the thickness and/or depth of nerves in a tissue and be able to distinguish between minor and major nerves.

In one embodiment, the nerve detector comprises a computing device 128 to convert received signals into information, including images and graphics, sent to the illuminated indicator. As mentioned above, the computing device may combine images or may use other methods of image processing. For instance, the computing device may combine 2D image slices at different focal planes or from different perspective angles in order to construct a 3D image. The computing device may then identify nerves in a tissue as well as their thickness and relative position. The computing device may then compare these properties within the image or with other images to distinguish between major nerves and minor nerves. Ultimately, the computing device may determine one or more locations within a tissue to inject an anesthetic drug proximal to a major nerve. In a similar manner, the computing device may be able to determine blood vessels or other tissues to avoid injection.

The computing device 128 may furthermore control anchor receive information from other optional parts of the syringe, such as a spectrometer 36 configured to detect an aspirate in the drug cartridge, a pressure sensor 130 on the plunger, a piston sensor 132 on the piston-engaging tip, a linear actuator 112 configured to drive the plunger position, a sensor configured to read information on an exterior of a drug cartridge, a wireless transceiver configured to transmit data to a computer or other device and/or some other mechanical or electrical device that works with the syringe. In other embodiments, a computing device may be electrically connected to the nerve detector but attached to the syringe in a location outside the nerve detector. For example, the computing device may be attached to the side of the syringe, or may be a part of the illuminated indicator or a transmitter.

Where the LED display indicates a real-time mapping of a nerve, that image mas be sufficient to indicate a direction for a medical professional to move the syringe without explicitly naming or showing a direction. For example, a medical professional may be able to see from an image that he or she needs to move the syringe to the 0.5 cm to the left, without the illuminated indicator explicitly indicating "left" or a relative distance. In another embodiment, the LED display may show both an image and explicitly indicate one or more directions to move the syringe.

Preferably where the linage is a real-time mapping of nerves or tissues, the display may also indicate a position of the tip or bevel of an attached needle, in order for a medical profession to determine the needle location in relation to the image. This may be done by overlaying a dot, a cross, or crosshairs onto the real-time mapping image. Alternatively, some part of the display may symbolize the distance between the needle tip and one or more preferred injection sites, without having to map the location of the needle. Alternatively, the LED display may be able to show two images side-by-side: one with a real time mapping of nerves, and the other image showing the needle location. In another embodiment, the display panel may comprise a semitransparent material, in order for a medical professional to observe a real-time overlay of an image, similar to what was mentioned previously for the illuminated indicator projecting an image.

In some cases, where different lengths of needles are used, the medical professional may need to calibrate the syringe so that the display correctly interprets the location of the needle tip. Alternatively, the type or length of needle may be inputted to a computing device in the syringe, or the nerve detector may be able to sense the location of the needle tip.

In one embodiment, the anesthetic syringe may comprise circuitry in order to compute its position, angle, and/or rotation along geometric coordinate axes. This information may be used to indicate a direction to move the syringe, and may be collaborated with data from the nerve detector. The anesthetic syringe may sense its position through one or more built-in instruments, including but not limited to an internal pendulum, a compass, an accelerometer, and/or a gyroscope. In a further embodiment, the anesthetic syringe may calculate its position from one or more external transmitters that wirelessly transmit position information.

In one embodiment, the display panel may be flexible. In this embodiment the display panel may bend against an exterior surface of a patient's tissue without poking, cutting, or otherwise causing harm to the patient. For example, when the anesthetic syringe is being used tor an oral nerve block, the screen may bend in contact with a patient's gum or inner cheek, without causing undue discomfort. In a related embodiment, the flexibility of the display panel may enable a medical professional to bend, fold, or roll the display panel out of his or her field of view prior to making an injection.

In one embodiment, the anesthetic syringe has a spectrometer attached to a side of the barrel, and the spectrometer is configured to detect blood in an aspirate. As defined herein, a spectrometer comprises a light source and a photodetector that together may characterize a portion of matter (solid, liquid, and/or gas) based on how the matter changes a property of the light. As defined herein, "light" refers to electromagnetic radiation within the ultraviolet, visible, or infrared wavelength ranges, which together span from 120 nm to 1 mm. The matter may change a property of the light such as intensity, direction, wavelength, and/or polarization. The spectrometer 36 may detect these changes using detection modes such as spectrophotometry, static light scattering, dynamic light scattering, fluorescence, polarization, and/or Raman scattering. The spectrometer comprises one or more photodetectors, and those photodetectors may modulate an electric signal in proportion with the intensity of an incident light, with or without specificity towards the wavelength or wavelengths of the light. For example, a single photodetector may generate a similar electric signal when exposed to light of a 280 nm wavelength as for light of a 700 nm wavelength of equal intensity, or it may generate different electric signals. Preferably the spectrometer 36 may detect blood within a portion of the cartridge near the first end of the syringe barrel 16, such as within 8-35 mm, preferably within 10-25 mm, more preferably within 12-22 mm of the membrane of an inserted drug cartridge, or at the end of an aspirating needle within the cartridge.

Preferably the spectrometer 36 may detect whole blood in an aspirate corresponding to a minimum concentration threshold of red blood cells per mL aspirate. The aspirate may be a concentrated stream entering the drug cartridge from an actively aspirating needle, or may be mixed and diluted by a drug solution within the drug cartridge. Preferably the concentration threshold is $10^8$ red blood cells/mL or less, preferably $10^6$ red blood cells/mL or less, more preferably $10^4$ red blood cells/mL or less. In one embodiment, the spectrometer may detect some other component of whole blood, such as plasma, platelets, and/or leukocytes. In one embodiment, the user may be able to raise or set a minimum concentration threshold. In other embodiments, a spectrometer measuring light scattering may be able to determine the velocity, volume, and/or particle size of an aspirate flowing into a drug cartridge. In other embodiments, a spectrometer may detect air bubbles within a drug cartridge.

In one embodiment, where the spectrometer 36 is a spectrophotometer, the spectrophotometer may be able to detect a change in absorbance for an incident light having a wavelength or wavelengths in the range of 200-1050 nm, preferably 300-800 nm, more preferably 400-680 nm. In one embodiment, the spectrophotometer may be tuned to a specific wavelength range corresponding to the absorption of whole blood and/or hemoglobin. This wavelength range may be 342-346 nm, 415-419 nm, 541-549 nm, and/or 573-580 nm. In some cases the wavelength ranges 208-212 nm, 276-280 nm, and/or 342-346 nm may be used for whole blood detection. Where the photodetector detects light scattering, it may measure light that is reflected back in the direction of the light beam, or deflected at an angle or range of angles, for instance, deflected 85°-95° relative to the transmission axis of the oncoming beam. In some embodiments, more than one type of photodetector may be present that together share a single light source or more than one light source. In other embodiments, different detectors may work in tandem, for instance, a photodetector for light scattering may be configured with circuitry to monitor for a sudden increase in scattering intensity. This increase in scattering intensity may be a sign of an aspirate, and may then trigger a spectrophotometric detector to take an absorption measurement to determine if the detected aspirate contains blood. In an alternative embodiment, the syringe and spectrometer may be configured to measure a property of an aspirate, with or without injecting a drug. For instance, a blood sample may be taken from a patient and measured within the syringe for hemoglobin concentration and/or oxygen saturation. Other body fluids may be collected and/or measured by the syringe, such as cerebrospinal fluid, bone marrow, and/or joint fluids. In a further embodiments the syringe may contain a compound for a colorimetric assay to determine other biomolecule concentrations, such as glucose. Other sensors may be used with the syringe, such as a pH sensor. In one embodiment, the needle may comprise a detector to detect the presence or absence of blood or to detect electric conductivity when inserted into a tissue. In one embodiment, a syringe may partially or completely fill a sample cartridge which may then be removed for further testing.

In an alternative embodiment, the light source may be external, such as light from ceiling lights, a separate instrument, a head lamp, a window, a flashlight, a flame, a lantern, and/or a mounted dental light. In this embodiment, the exterior of the syringe barrel preferably comprises at least one opening 32 to allow the external light to enter the cartridge. In a further embodiment, this opening may be large enough for a user to also see blood aspirated into the cartridge. In one embodiment, the syringe barrel may comprise a sliding cover 34 or covers that may expose one or more areas of the cartridge to external light. In one embodiment, the light source may comprise a gas discharge lamp, an incandescent bulb, a laser, and/or a light emitting diode (LED). The light source may be connected to the spectrometer 36 by a fiber optic cable to allow illumination near the first end of the syringe barrel, for example, within 8-35 mm, preferably within 10-25 mm, more preferably within 12-22 mm of the membrane of an inserted drug cartridge while using less space than directly attaching the light source near the first end of the syringe barrel. In an alternative embodiment, the light source may be a gas discharge lamp (such as a mercury vapor lamp, a xenon lamp, an argon lamp, or a metal halide lamp), a laser, and/or an incandescent bulb housed in a casing separate from the syringe but attached by a fiber optic cable.

In a further embodiment, the anesthetic syringe with the spectrometer has a second illuminated indicator 106 on an exterior side of the barrel. This second illuminated indicator is electrically connected to the spectrometer to indicate if blood has been detected during aspiration. In a further embodiment, there may be a third illuminated indicator 108 on an exterior side of the barrel, also electrically connected to the spectrometer 36, and which indicates if blood has not been detected during aspiration. Preferably these lights are located on the side of the barrel near the first end of the barrel 16, within the first 50%, preferably the first 40%, more preferably the first 30% of the length of the barrel adjacent to the first end. Preferably one or both of the lights are LEDs, though other types of electric lights may be used. Preferably the lights are located where they may not be obscured by the hand of a person holding the syringe. In one embodiment, the lights may be located near the second end of the barrel, or elsewhere on the syringe housing, for example, at the end of the syringe housing opposite to the needle mount, as in FIGS. 3 and 4. In one embodiment, a single, multi-colored light may be used to indicate either the presence or absence of blood. In another embodiment, one or more indicator lights may be scaled by intensity or form a number in order to indicate the certainty of detecting blood, or the strength of an absorption measurement and/or a light scattering measurement, and/or a battery capacity. In one embodiment, a third illuminated indicator may be used to indicate that an aspirate has been detected, but blood has not been detected. Alternatively, a fourth or other illuminated indicators could indicate if the absorbance or light scattering values are too low, too high, or out of a specific range. This may indicate that a light source and/or photodetector are malfunctioning and/or unintentionally blocked. In another embodiment, additional indicator lights 110 may be placed on the exterior of the syringe barrel and/or syringe housing, and may be in different locations than a second and/or third illuminated indicator. In an alternative embodiment, the anesthetic syringe may have speakers 622 to generate certain sounds or melodies in order to convey similar information from the spectrometer relating to blood in the aspirate.

However, in one alternative embodiment, the nerve detector and/or some other detector may be able to locate blood vessels in a tissue. A user of the anesthetic syringe may easily avoid placing the needle in a blood vessel with this information, thus rendering any aspirating mechanism or spectrometer unnecessary.

As mentioned previously, the plunger of the anesthetic syringe may be driven by a motor. In one embodiment, the anesthetic syringe has a linear actuator 112 and an electric motor 114 to slide the plunger 18 within the hollow syringe barrel interior 42. In this embodiment, the entire plunger may be contained within the hollow syringe barrel and/or a syringe casing 28, or the end distal the piston-engaging tip may protrude from the syringe barrel and/or casing. The linear actuator is a mechanism or set of mechanisms that convert the rotational motion of the motor into translational motion on the plunger. Preferably the electric motor runs on DC power. The power for the motor may be supplied by a rechargeable and/or replaceable battery housed in the syringe casing, or by an external power line or AC adaptor. The electric motor may be a brushed or brushless DC motor, a switched reluctance motor, a universal motor, a stepper motor, a servomotor, an axial rotor motor, or some other type of motor. In an alternative embodiment, the motor may be an AC asynchronous motor, such as a shaded pole motor, or an AC synchronous motor, such as a hysteresis motor, or some other AC motor. Preferably, a gear train may exist to reduce the rotational motion coming directly from the electric motor. The gear train may have a double gear with a bevel edge 116 that connects with a bevel gear 118 on the motor shaft. The connection of these two gears allows the motor to be placed with its rotational axis parallel with the longitudinal axis of the syringe barrel, so that the motor dries not significantly protrude. The double gear with the bevel edge 116 may drive one or more double gears 120, one of which may connect to a linear actuator 112. The linear actuator may be a lead screw, a belt drive, a worm drive, a rack and pinion drive, a chain drive, or some combination thereof.

In some embodiments, a side of the plunger may be attached to a linear actuator. For example, the end of the plunger distal the piston-engaging tip may be attached to a chain in a chain drive mechanism or to a lead screw in a traveling screw mechanism. In FIGS. 3 and 4, a plunger 18 is connected to a chain drive. Here, a double gear 120 comprises a chain sprocket to drive a chain 122 within the syringe. A side of the plunger 18 is attached to the chain 122 and the plunger is held in position by guide wheels 124. So one embodiment where the plunger is moved by a motor or other mechanical means, a bushing 44 may be sufficient to support the position of the plunger. Preferably an electric motor and linear actuator are able to move a plunger to engage the piston-engaging tip with a piston of a drug cartridge, and move the piston towards the membrane-capped end of the drug cartridge until coming into contact with the membrane or neck of the drug cartridge, or a needle inserted into the drug cartridge. Preferably an electric motor and linear actuator are able to move a piston in the opposite direction away from the membrane-capped end of a drug cartridge.

In other embodiments, the plunger 18 may be directly involved as a mechanical part of a linear actuator, for instance, a surface of the plunger parallel with its central axis may comprise gear teeth in order to form a rack for a rack and pinion drive. For example, the teeth of the inner gear of a double gear may mesh with the teeth along the length of a plunger Alternatively, other actuators may be used, with or without rotational motion from a motor. For instance, the end of the plunger distal to the piston-engaging tip may comprise a hydraulic or pneumatic piston, so that the translational motion of the piston is controlled by air or fluid pressure. Alternatively, the plunger may be driven by a linear electric motor, or by the energy contained in a wound-up or compressed spring. In one embodiment, a plunger may be attached and movable by a linear actuator and electric motor, but also have a thumb rest to allow for manual movement of the plunger. In some embodiments, a sensor, a structure, and/or a device in the motor, syringe barrel, and/or linear actuator may prevent the motor from pushing the plunger beyond certain lengths in the syringe. In a further embodiment, a feedback mechanism or circuitry exists in the syringe barrel or in the motor that can tell the position of the plunger. In another related embodiment, optical, magnetic, electric, acoustic, or mechanical sensors may exist along the interior of the syringe barrel in order to detect the position of the plunger and/or the piston. In one alternative embodiment, a drug cartridge and plunger may be located in a separate module connected to a handle by flexible tubing that carries the drug. Here, the handle may comprise a needle and a spectrometer.

In a further embodiment, the anesthetic syringe may have a button or a switch 126 on an exterior side of the barrel electrically connected to an electric motor 114. The button or switch on the side of the syringe may control the position of the plunger towards or away from the first end, and there may be more than one button or more than one switch. In other embodiments, a button or switch may turn the syringe on or off, or start an automatic aspiration and/or injection routine. Preferably the button or switch is positioned on the syringe where a user can access the button without changing his or her grip on the syringe. In an alternative embodiment, a foot pedal electrically attached to the motor may provide the same control, or a foot pedal may control the motor through a wireless transceiver. The button, switch, and/or foot pedal control may move the plunger at a single speed in each direction or at variable speeds. In one embodiment, an indicator light may comprise a button or a switch.

As mentioned previously, anesthetic syringe may have a computing device 128 as part of the nerve detector or separate from the nerve detector. This computing device may control the illuminated indicator as mentioned previously, and may analyze signals received by the nerve detector. The computing device 128 may also control parts comprising the nerve detector 26, such as the positions of a focusing lens 62, the adjustable pinhole 68 diameter, the movement of rotating and/or pivoting reflectors 66, and the rotation of a Nipkow disk 70, where applicable. Where an anesthetic syringe comprises a motor-driven plunger, the computing device 128 may also be able to receive a signal from a spectrometer 36, button, or switch 126 and send an output signal to power the electric motor 114 to actuate the plunger 18. In this embodiment preferably a feedback mechanism exists for the computing device to detect the position of the plunger. The feedback mechanism may involve a calibration step, such as moving the plunger between two limits of a range of positions within the hollow syringe barrel, before a user loads a drug cartridge. In some embodiments, the computing device may send a signal to turn on and/or control the spectrometer.

Next, a hardware description of the computing device 128 according to exemplary embodiments is described with reference to FIG. 6. Here, the computing device 128 includes a CPU 600 which performs the processes described above below. The process data and instructions may be stored in memory 602. These processes and instructions may also be stored on a digital storage medium 604 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk, solid-state drive, and/or any other information processing device with which the computing device communicates, such as a server or computer. In one embodiment, the digital storage medium 604 comprises a memory card that can be removed and exchanged. The digital storage medium of the computing device may have a formatted capacity of 1 MB-10 GB, preferably 10 MB-5 GB, more preferably 100 MB-4 GB.

Further, the claimed advancements may be provided as a utility application, background daemon, or component of an operating system, or combination thereof, executing in conjunction with CPU 600 and an operating system such as Microsoft Windows 7, UNIX, Solaris, LINUX, Apple macOS, and other systems known to those skilled in the art.

The hardware elements of the computing device may be realized by various circuitry elements, known to those skilled in the art. For example, CPU 600 may be a Xenon or Core processor from Intel of America or an Opteron processor from AMD of America, or may be other processor types that would be recognized by one of ordinary skill in the art. Alternatively, the CPU 600 may be implemented on an FPGA, ASIC, PLD, or the CPU may use discrete logic circuits, as one of ordinary skill in the art would recognize. Further, the CPU 600 may be implemented as multiple processors cooperatively working in parallel to perform the instructions of the inventive processes described above and below.

Figure 6:
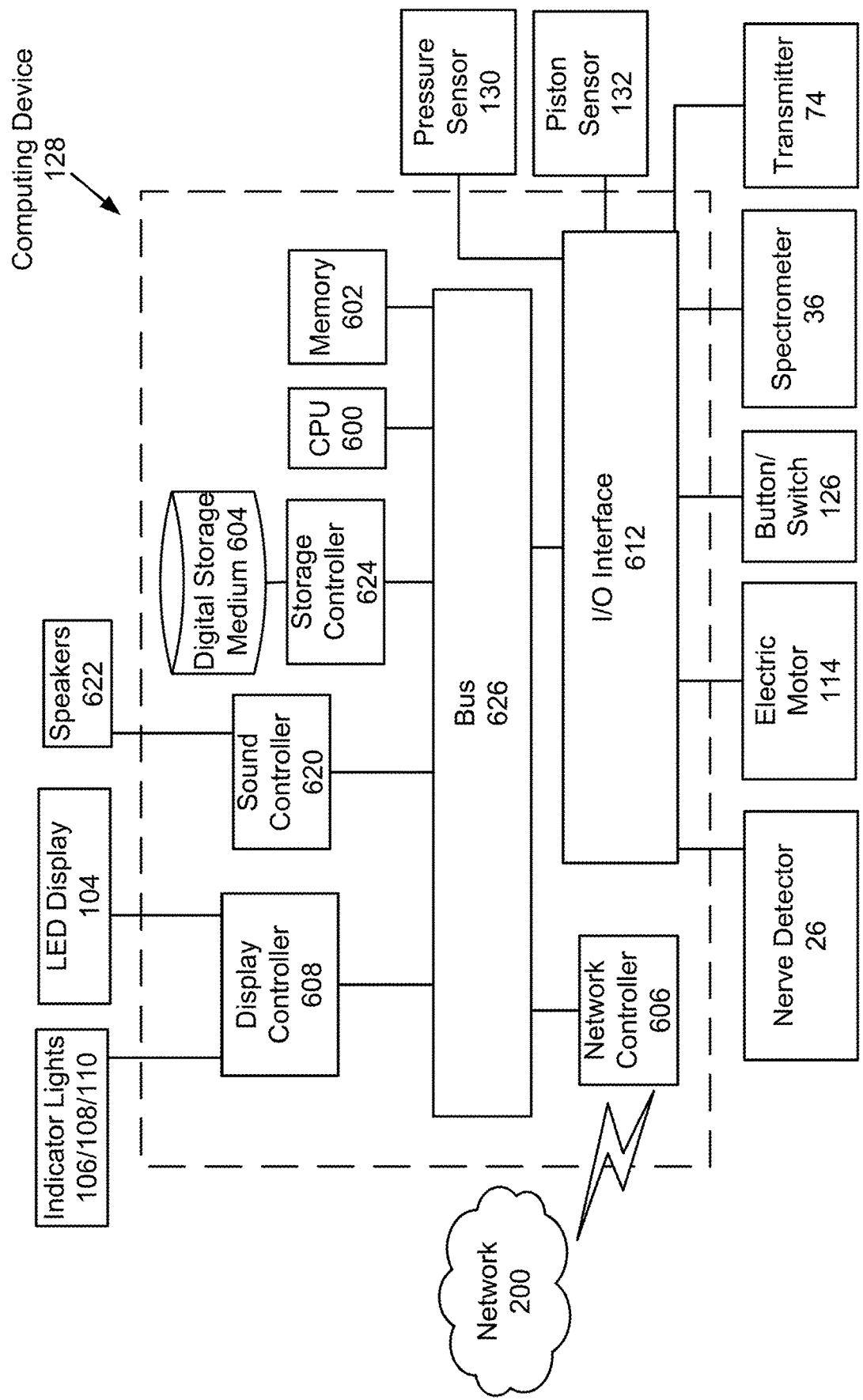
FIG. 6 is a diagram of a computing device connected to components of an anesthetic syringe.

The computing device in FIG. 6 may also include a network controller 606, such as an Intel Ethernet PRO network interface card from Intel of America, for interfacing with a network 200. As can be appreciated, the network 200 may be a public network, such as the Internet, or a private network such as an LAN or WAN network, or any combination thereof, and may also include PSTN or ISDN sub-networks. The network 200 can also be wired, such as an Ethernet network, or can be wireless such as a cellular network including EDGE, 3G, and 4G wireless cellular systems. The wireless network can also be WiFi, Bluetooth, ANT, DASH7, ISA100.11a, MiWi, near-field communication, OCARI, ONE-NET, TSMP, WirelessHART, ZigBee, Z-Wave, and/or any other known form of wireless communication.

The computing device 128 may include a display controller 608, such us a NVIDIA GeForce GTX or Quadro graphics adaptor from NVIDIA Corporation of America. The display controller 608 may interface with the illuminated indicator on the syringe, such as an LED display 104. The display controller 608 may also interface with indicator lights 106/108/110 on the syringe. A general purpose I/O interface 612 may interface with switches or buttons 126 on the syringe, with the spectrometer 36, with the nerve detector 26, with an electric motor 114, with a transmitter 74, with a piston sensor 132 in the piston-engaging tip, and/or with a pressure sensor 130 in the plunger.

A sound controller 620 may be provided in the computing device 128, such as Sound Blaster X-Fi Titanium from Creative, to interface with speakers 622 to provide alerting sounds or melodies.

A general purpose storage controller 624 may connect to a digital storage medium 604 with communication bus 626, which may be an ISA, EISA, VESA, PCI, or similar, for interconnecting all of the components of the computing device 128.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset.

The computing device 128 may be electrically connected to a pressure sensor in the plunger 18 and/or a sensor in the piston-engaging tip 22. For example, in one embodiment the piston-engaging tip may have a sensor 132 configured to detect if the piston-engaging tip 22 is engaged within a piston of a drug cartridge. This sensor may be a mechanical switch on an exterior surface of a harpoon. When the harpoon is not engaged in a piston, the switch may protrude from the harpoon surface, and while engaged within a piston, the switch may lie against the surface of the harpoon, or in a different position. These two configurations of the switch may correspond to opening or closing a circuit, which may send a signal to the computing device. In an alternative embodiment, the switch on the harpoon may provide a catch that holds the harpoon within the piston, and following an injection, the switch may have a mechanism to withdraw itself into the harpoon so that the harpoon can more easily be removed from the piston. Alternatively, the sensor may be a piezoelectric element which creates a change in electric charge when under pressure, or the sensor may be piezoresistive, electromagnetic, and/or inductive, or the sensor may be able to modify some other property of electricity, magnetism, and/or electromagnetic radiation. In an alternative embodiment, the harpoon may comprise a pressure sensor relying on hydraulics, pneumatics, and/or optics. In one embodiment, the harpoon may comprise more than one type of sensor, or the plunger or second cylinder may comprise a sensor that can similarly tell if the piston is engaged.

As mentioned above, in one embodiment, the plunger 18 has a pressure sensor 130. Preferably this pressure sensor may be configured to measure the pressure being applied from the plunger to a piston, after the piston-engaging tip is engaged in the piston. This pressure sensor may be piezoelectric, piezoresistive, or a sensor of another type as listed previously. The pressure sensor may be located anywhere along the length of the plunger, but preferably the sensor is located on a portion of the plunger closer to the piston-engaging tip, for example, within 5-15 mm, preferably within 7-13 mm, more preferably within 7-12 mm of the piston-engaging tip. Preferably the pressure sensor may detect a positive or negative pressure of an absolute value of at least 500 Pa, preferably at least 100 Pa, more preferably at least 10 Pa. In one embodiment, the pressure sensor may detect a certain absolute pressure on the plunger, for example, 60-200 kPa, and send a signal to the computing device and/or an indicator light to indicate malfunction. In one embodiment, a user may adjust certain pressure thresholds in order to stay within a certain pressure range, or trigger an alert at different pressures.

In one embodiment the computing device may record a position of the plunger within the syringe barrel. Where the computing device senses and records two positions of the plunger, it may calculate a corresponding change in the cartridge volume. The computing device may record other information delivered to it by other sensors. This information may relate to changes in injection pressure, values of spectrometer readings, time and date, the identity of the drug injected, and/or other parameters mentioned previously.

According to a second aspect, the present disclosure relates to a method of administering a nerve block to a nerve in a patient using the anesthetic syringe of the first aspect. The method may involve loading a drug cartridge containing an anesthetic drug into the anesthetic syringe 10, and attaching an anesthetic syringe needle to the needle mount 14. Alternatively, the anesthetic syringe may be pre-loaded with a drug cartridge and/or with an anesthetic syringe needle pre-attached to the needle mount. The method involves the nerve detector 26 receiving a radiative energy from a nerve, preferably from a nerve to which the anesthetic should be delivered. In some embodiments, as mentioned previously, a transmitter 74 located on the syringe or elsewhere may be used to radiate the nerve prior to or while receiving a radiative enemy from the nerve. The illuminated indicator 24 of the syringe then indicates a direction to move the anesthetic syringe to a location proximal to the nerve. The illuminated indicator may show an arrow or a distance to move the syringe, and/or may show a real-time mapping of nerves or other tissues in relation to the syringe. In some embodiments, the indicated direction may take into account other parameters, such as other tissues to avoid, such as blood vessels, or the length of the attached needle. The syringe may then be moved in the direction suggested by the illuminated indicator. Preferably the illuminated indicator is able to update or refresh itself until the desired position is achieved. Then, the needle may be inserted into the tissue proximal to the nerve, and an anesthetic injection of the anesthetic drug may be performed. Depending on the design of the syringe, a display panel or arm-mounted display panel on the syringe may be moved out of the way or detached from the syringe prior to inserting the needle or prior to injecting the anesthetic drug. In an alternative embodiment, a marking element on a syringe without a needle may be used to mark the exterior surface of a tissue at an injection site. Then, the needle may be attached and inserted into the marked tissue location.

As mentioned previously, where an anesthetic syringe is able to detect the location of blood vessels, its illuminated indicator may indicate a direction or mapping of blood vessels to avoid injection. In this embodiment, the anesthetic drug may be injected without aspiration. In other cases, once a needle is inserted into a tissue, the method may further comprise the steps of aspirating an aspirate into the drug cartridge to detect the presence or absence of blood. In the embodiment where the piston-engaging tip is a harpoon or similar shape, the harpoon may be inserted into the piston before aspirating. A user may aspirate the syringe by moving the plunger away from the needle mount. In some cases, a user may first need to eject a volume of the drug from the drug cartridge in order to have the available space to aspirate by moving the piston away from the needle. For a manual self-aspirating syringe, aspiration may be performed by applying moderate pressure to the plunger or to a bushing in order to push a drug cartridge forward and deform the membrane of the drug cartridge. An annular stud or other shape may project into the barrel interior in order to deform the membrane. Releasing the pressure on the cartridge restores the membrane shape and creates a negative pressure within the cartridge, which withdraws an aspirate through the needle. In some instances, a user may insert a needle into a tissue of a patient and aspirate at more than one needle depth prior to injecting a drug. Detecting aspirates from more than one needle depth at a specific injection point may help a user avoid injecting into a patient's blood vessel.

This detection of blood in the aspirate may be done visually or by an optional spectrometer 36 attached to a side of the syringe barrel. Detection by the spectrometer may send a signal to the illuminated indicator or indicator lights to alert the presence or absence of blood, and the thresholds of this detection may be modified in advance by a user. If no blood is detected, the drug may be injected at that needle location. Otherwise, the needle is removed from the tissue and placed in a different location of tissue, with or without guidance from the nerve detector and illuminated indicator. In embodiments where a plunger is driven by an electric motor, sensors on the plunger and/or piston-engaging tip may enable the electric motor to automatically slide the plunger to engage the piston-engaging tip within the piston of a loaded drug cartridge. This may provide automation of certain aspiration steps. For example, having attached a needle to the needle mount, a user may stick the needle into a tissue of a patient and press a switch or other control on the syringe to begin an aspiration process. The motor may then move the plunger and the piston away from the first end to create an aspirate in the drug cartridge, and a light may signal if blood is or is not detected in the aspirate by the spectrometer. In one embodiment, the syringe may next automatically inject a volume from the drug cartridge if blood is not detected. In another embodiment, a syringe may aspirate automatically, and then prompt a user to choose to aspirate again or to inject a volume from the drug cartridge. Using feedback from the pressure sensor on the plunger and the plunger's position relative to the drug cartridge, the computing device may be able to control the electric motor to inject at a constant pressure or a constant flow rate. The motor may be able to stop once a certain volume has been injected or aspirated. In another embodiment, the motor may be able to inject at a slowly increasing pressure and/or speed, in order to reduce pain to a patient. In some embodiments of syringes capable of automatic aspiration, a button or switch may exist for a user to override an automatic step and instead directly control the electric motor.

In one embodiment, where the anesthetic syringe has a motor-driven plunger and spectrometer, the anesthetic syringe also has red light and a button comprising a green light, where the lights are attached to the side of the syringe barrel or to the second end. Here, a syringe with a needle attached to the needle mount and loaded with a drug cartridge may be inserted into an injection site. The automatic aspiration will be triggered by pressing an aspiration button or other control, and the syringe will aspirate. The spectrometer will check for the presence of blood in the aspirate, and where blood is not detected the green light will turn on. At this time the user may press the green light button to begin an automatic injection of the contents of the drug cartridge. Where the spectrometer detects blood, the red light will illuminate or flash, and the automatic injection will be momentarily suspended, which disables the green light button. In a further embodiment, the button comprising the green light may be on the side of the syringe barrel, with the red light located at the second end of the syringe barrel. In one alternative version of this embodiment, the syringe has a motor-driven plunger, a spectrometer, and the lights and buttons as mentioned previously, but does not have a nerve detector.

With certain syringe embodiments, a user relatively unskilled in performing a nerve block with a manual syringe may be able to easily locate injection sites with the illuminated indicator and automatically perform an injection of a drug with or without aspiration. The procedure and automatic embodiments of the syringe may further be adapted to a syringe-handling robot. Such a robot could appropriately maneuver a syringe to an injection site and perform the automatic injection. Alternatively, a robot may be partially guided by a person, as in remote surgery.

The invention claimed is:

1. An anesthetic syringe comprising:
   a hollow syringe barrel with a needle mount extending outwards from a first end of the hollow syringe barrel;
   a plunger extending from a second end of the hollow syringe barrel and slidably moveable within the hollow syringe barrel; the plunger having a piston-engaging tip extending into the hollow syringe barrel;
   a first illuminated indicator directly attached to an exterior part of the hollow syringe barrel or mounted to an arm directly attached to the exterior part of the hollow syringe barrel;
   a transmitter configured to emit an emitted radiative energy onto a nerve;
   a nerve detector directly attached to the first illuminated indicator or directly attached to a second exterior part of the hollow syringe barrel, the nerve detector configured to receive an incoming radiative energy from the nerve;
   a spectrometer attached to and in direct contact with an interior side of the hollow syringe barrel,
   wherein the spectrometer is configured to detect blood in an aspirate;
   a second illuminated indicator on an exterior side of the hollow syringe barrel and electrically connected to the spectrometer to indicate if blood has been detected during aspiration; and
   wherein the first illuminated indicator is electrically connected to the nerve detector and is configured to receive a signal from the nerve detector and indicate at least one direction to move the anesthetic syringe to deliver an anesthetic injection proximal to the nerve,
   wherein the incoming radiative energy is not visible light and is not an electric field, and
   wherein the first illuminated indicator comprises:
   a first display panel mounted to a first arm, the first arm directly attached to the exterior part of the hollow syringe barrel, and
   a second display panel mounted to a second arm, the second arm directly attached to the exterior part of the hollow syringe barrel.

2. The anesthetic syringe of claim 1 wherein the nerve detector is directly attached to the first illuminated indicator.

3. The anesthetic syringe of claim 1 wherein the transmitter is directly attached to the first illuminated indicator.

4. The anesthetic syringe of claim 1 which does not have an ultrasonic transmitter.

5. The anesthetic syringe of claim 1 wherein the first illuminated indicator is slidably and/or pivotally attached to the hollow syringe barrel.

6. The anesthetic syringe of claim 1 wherein the nerve detector comprises two or more photodetectors.

7. The anesthetic syringe of claim 1, wherein the first display panel comprises at least 625 LEDs.

8. The anesthetic syringe of claim 1, wherein the arms are removably attached to the exterior part of the hollow syringe barrel.

9. The anesthetic syringe of claim 1, wherein the first display panel is positioned outwards from the first end of the hollow syringe barrel and shaped with a hole or a slot to accommodate a needle attached and extending outwards from the needle mount, the needle traversing the first display panel through the hole or the slot.

10. The anesthetic syringe of claim 1, wherein the first display panel and the second display panel are positioned outwards from the first end of the hollow syringe barrel and are shaped to accommodate a needle attached and extending outwards from the needle mount.

11. The anesthetic syringe of claim 1, wherein the incoming radiative energy is electromagnetic radiation.

12. A method of administering a nerve block to a nerve in a patient with the anesthetic syringe of claim 1, the method comprising:
   emitting the emitted radiative energy to the nerve by the transmitter;
   receiving the incoming radiative energy from the nerve by the nerve detector;
   indicating a direction to move the anesthetic syringe to a location of a tissue proximal to the nerve by the first illuminated indicator;
   moving the anesthetic syringe to the location of the tissue proximal to the nerve; and
   inserting a needle mounted onto the needle mount of the anesthetic syringe into the location of the tissue proximal to the nerve, wherein the anesthetic syringe is loaded with a drug cartridge comprising an anesthetic drug; and
   performing an anesthetic injection of the anesthetic drug.

* * * * *